(12) United States Patent
Li et al.

(10) Patent No.: US 8,530,183 B2
(45) Date of Patent: Sep. 10, 2013

(54) ZINC SENSORS FOR CELLULAR IMAGING

(75) Inventors: Wen-Hong Li, Dallas, TX (US);
Daliang Li, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 279 days.

(21) Appl. No.: 13/158,011

(22) Filed: Jun. 10, 2011

(65) Prior Publication Data
US 2012/0009617 A1    Jan. 12, 2012

Related U.S. Application Data

(60) Provisional application No. 61/353,477, filed on Jun. 10, 2010.

(51) Int. Cl.
*C12P 1/02* (2006.01)
(52) U.S. Cl.
USPC ...... 435/29; 435/4; 546/12; 546/24; 546/153; 546/159; 546/256
(58) Field of Classification Search
USPC .................. 435/4, 29; 546/12, 24, 153, 159, 546/256
See application file for complete search history.

(56) References Cited

U.S. PATENT DOCUMENTS

| 2005/0037332 A1* | 2/2005 | Komatsu et al. | 435/4 |
| 2005/0112769 A1 | 5/2005 | Lippard et al. | 436/81 |
| 2005/0182253 A1* | 8/2005 | Yano et al. | 540/474 |

FOREIGN PATENT DOCUMENTS
WO   WO 2011019864 A2 *  2/2011

OTHER PUBLICATIONS

International Search Report and Written Opinion, issued in PCT/US2011/040005, dated Nov. 30, 2011.
Frederickson, et al., "The neurobiology of zinc in health and disease," *Nat. Rev. Neurosci.*, 6:449-62, 2005.
Gee, et al., "Detection and imaging of zinc secretion from pancreatic beta-cells using a new fluorescent zinc indicator," *J. Am. Chem. Soc.*, 124:776-8, 2002.
Kasai, et al., "A new quantitative (two-photon extracellular polar-tracer imaging-based quantification (TEPIQ)) analysis for diameters of exocytic vesicles and its application to mouse pancreatic islets," *J. Physiol.*, 568:891-903, 2005.
Komatsu, et al., "Selective zinc sensor molecules with various affinities for Zn2+, revealing dynamics and regional distribution of synaptically released Zn2+ in hippocampal slices," *J. Am. Chem. Soc.*, 127:10197-204, 2005.
Michael, et al., "Human insulin vesicle dynamics during pulsatile secretion," *Diabetes*, 56:1277-88, 2007.
Nagamatsu, "TIRF microscopy analysis of the mechanism of insulin exocytosis," *Endocr. J.*, 53:433-40, 2006.
Qian, et al., "Imaging of Zn2+ release from pancreatic beta-cells at the level of single exocytotic events," *Anal. Chem.*, 75:3468-75, 2003.
Que, et al., "Metals in Neurobiology: probing their chemistry and biology with molecular imaging," *Chem. Rev.*, 108:1517-49, 2008.

\* cited by examiner

*Primary Examiner* — Susan Hanley
(74) *Attorney, Agent, or Firm* — Parker Highlander PLLC

(57) ABSTRACT

The present invention provides compounds for use as zinc ligand sensors in cellular imaging. These compounds are sensitive imaging agents that can be used with techniques such a laser scanning microscopy in intact cells in culture or in tissue preparations.

27 Claims, 12 Drawing Sheets

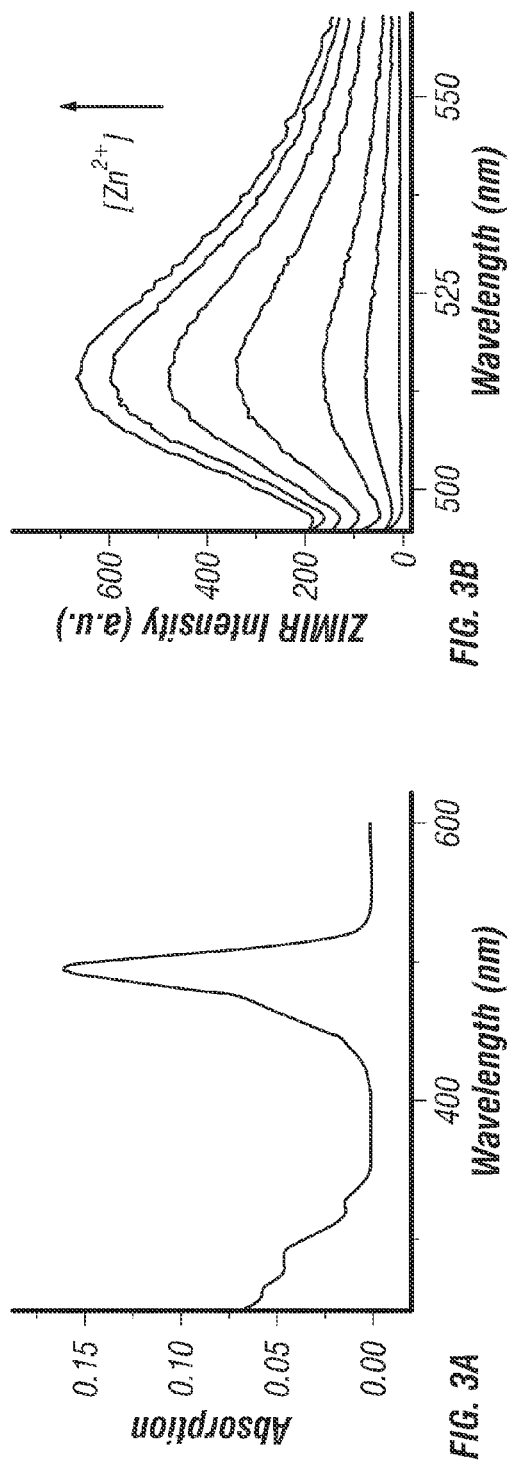
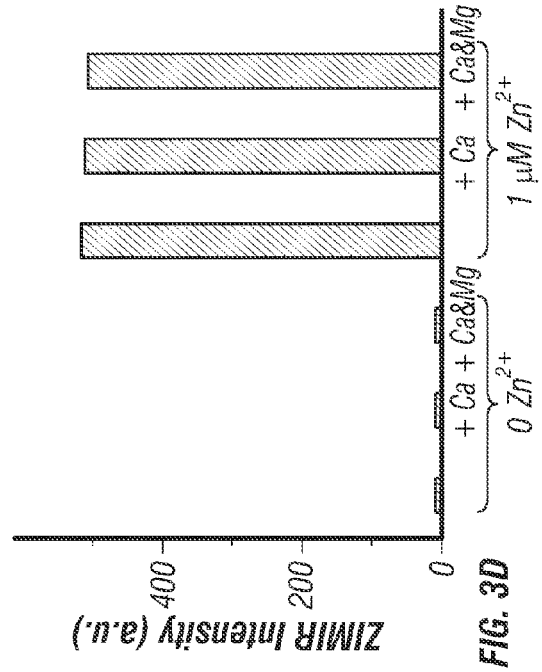
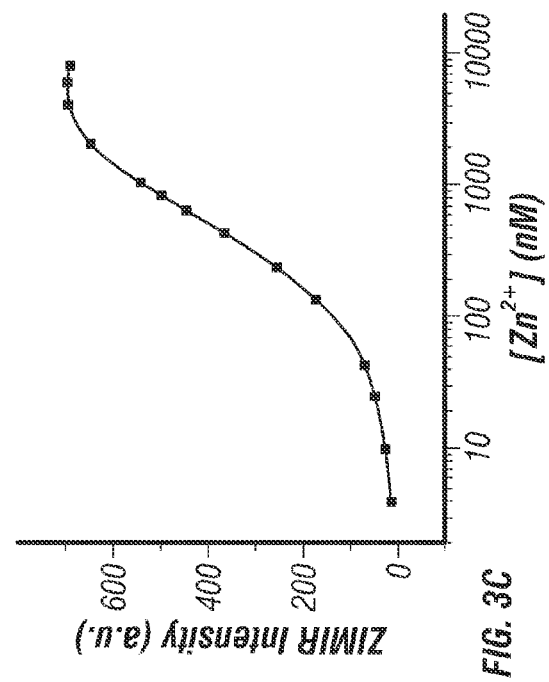
FIG. 3A
FIG. 3B
FIG. 3C
FIG. 3D

ZINC SENSORS FOR CELLULAR IMAGING

This application claims benefit of priority to U.S. Provisional Application Ser. No. 61/353,477, filed Jun. 10, 2010, the entire contents of which are hereby incorporated by reference.

This invention was made with government support under grant number 5R01GM077593 awarded by the National Institutes of Health. The government has certain rights in the invention.

BACKGROUND OF THE INVENTION

I. Field of the Invention

The present invention relates generally to the field of cellular biology and imaging, and more specifically relates to new zinc sensing compounds and their use in microscopy, cytometry and spectroscopy for the detection of zinc ion release by cells in normal and pathologic states.

II. Description of Related Art

A variety of mammalian cells, including the pancreatic beta cells (Falkmer and Pihl, 1968; Kristiansen et al., 2001), submandibular salivary gland (Frederickson et al., 1987), the prostate epithelial cells (Sorensen et al., 1997), paneth cells in the crypts of Lieberkühn (Giblin et al., 2006; Muller and Geyer, 1969), mast cells (Gustafson, 1967; Ho et al., 2004), granulocytes (Goldberg et al., 1993; Ieshchenko et al., 1994), pituitary cells (Thorlacius-Ussing, 1987), and certain neurons of the central nervous systems (Birinyi et al., 2001; Haug, 1967), etc., contain zinc ion ($Zn^{2+}$) in their secretory granules. Upon stimulation, these cells release the contents of their secretory granules into extracellular medium, during which $Zn^{2+}$ is co-released (Frederickson et al., 2005).

FluoZin-3 is the first fluorescent $Zn^{2+}$ sensor reported for monitoring $Zn^{2+}$/insulin release in cultured beta cells (Gee et al., 2002). Since FluoZin-3 is applied to the extracellular bath, the sensitivity of detecting local Zn2+ release near the plasma membrane is compromised by the background fluorescence from the bulk solution. Consequently FluoZin-3 imaging has been largely limited to the use of total internal reflection of fluorescence (TIRF) microscopy in order to study secretion at the interface between a cell and the underlying glass coverslip (Michael et al., 2006). Also, FluoZin-3 binds to $Zn^{2+}$ with nanomolar affinity ($Zn^{2+}$ dissociation constant $K_d(Zn^{2+})=15$ nM), but it also binds $Ca^{2+}$ with a $K_d(Ca^{2+})$ of about 10 µM. Since extracellular $Ca^{2+}$ concentration is higher than 1 mM, $Ca^{2+}$ effectively competes $Zn^{2+}$ for FluoZin-3 binding, thus limiting the capacity of FluoZin-3 to sense $Zn^{2+}$. Further, since FluoZin-3 also binds to other heavy metal ions with high affinity, assaying buffers have to be prepared from the highest grade of salts available and treated with the Chelex resin to remove contaminating heavy metals (Qian et al., 2003). These limitations lower the sensitivity of $Zn^{2+}$ detection, complicate and lengthen the assaying process, and discourage the routine application of the assay.

Another reported imaging assay of insulin release relies on transfecting cells with GFP tagged insulin or C-peptide. When these fluorescent fusion proteins are expressed in cells, they are incorporated into insulin secretory granules. Exocytosis of these labeled proteins can be captured by total internal reflection fluorescence (TIRF) microscopy (Michael et al., 2007; Nagamatsu, 2006; Ohara-Imaizumi et al., 2002). Since TIRF imaging only detects fluorescence signal at the cell membranes that directly contact a glass coverslip, this method cannot provide information about secretion in 3 dimensions, thus preventing studying exocytosis of cells in the organotypic culture or in the intact islet where normal cell-cell contact is maintained. Further, since the assay relies on transfection and expression of fusion proteins which typically takes 24-48 hours, primary beta cells (including primary human beta cells) may alter their secretory behavior during this time in culture.

In two photon extracellular polar tracer imaging (TEP) (Kasai et al., 2005), islets are immersed in a solution containing a polar, membrane impermeant tracer such as sulforhodamine-B (SRB). Since the assay was based on changes in membrane morphology (forming Ω shaped membrane profile) during secretion, its fluorescence readout is susceptible to artifacts caused by motion or by membrane extension, retraction or ruffling that is unrelated to exocytosis. Further, the assay only detects the dye filling of secretory granules, which does not necessarily correlate with the insulin release activity.

Thus, although a number of techniques exist to detect $Zn^{2+}$ release in intact cells, each of these has distinct limitations and disadvantages. New and improved compositions and methods for cellular imaging of zinc ion release are therefore needed.

SUMMARY OF THE INVENTION

Thus, in accordance with the present invention, there is provided a method of detecting zinc ion ($Zn^{2+}$) release by a cell comprising (a) contacting a cell with a compound having the formula:

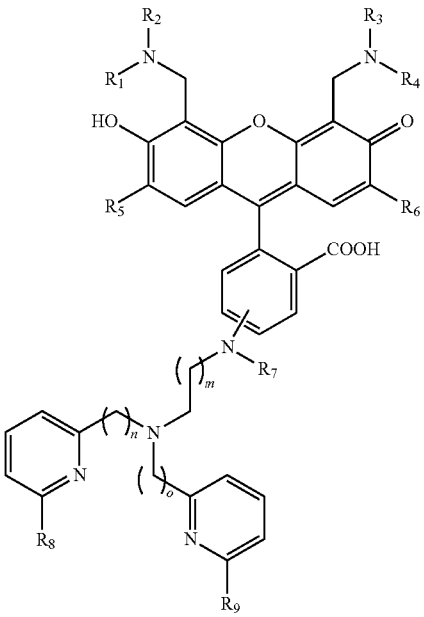

wherein
$R_1$ and $R_4$ are independently H, or —$CH_2(CH_2)_aCOOH$, $CH_2(CH_2)_bSO_3H$, wherein a=0-2 and b=1-3;
$R_2$ and $R_3$ are independently H, or linear or branched $C_{1-20}$ alkyl;
$R_5$ and $R_6$ are independently H, F, Cl, Br;
R7 is H, or linear or branched $C_{1-4}$ alkyl or acetate;
R8 and R9 are independently H, or linear or branched $C_{1-4}$ alkyl or acetate; and
m=1-3; n=1-4; and o=1-4;
and pharmaceutically acceptable salts thereof, and (b) detecting fluorescence of said compound following zinc release by said cell and binding of zinc by said compound. $R_5$, $R_6$, $R_7$, $R_8$ and $R_9$ may be m and n may be 1 and o may be 2. More particularly, $R_1$ and $R_4$ may be the same, and or $R_2$ and $R_3$ may be the same. $R_1$ and $R_4$ may be —$CH_2COOH$ and/or $R_2$ and $R_3$ may be —$CH_2CH_3$ or —$(CH_2)_{11}CH_3$.

The cell may be a pancreatic beta cell, a submandibular salivary gland cell, a prostate epithelial cell, a paneth cell, a mast cell, a granulocyte, a pituitary cell, a or a CNS neuron. Detecting may comprise confocal laser scanning microscopy, two photon laser scanning microscopy, or total internal reflection fluorescence microscopy. The cell may be an isolated cell, such as in culture, or in an intact tissue, such as an isolated pancreatic islet. The method may further comprise detecting fluorescence at multiple time points. The method may further comprise stimulating said cell with a zinc ion release agent. The concentration of said compound may be between 1 nM and 100 μM, or between 5 nM and 1 μM.

In another embodiment, there is provided a compound having the formula:

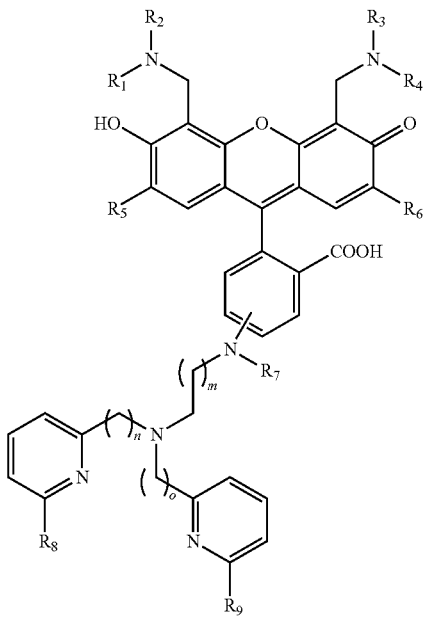

wherein $R_1$ and $R_4$ are independently H, or —$CH_2(CH_2)_aCOOH$, $CH_2(CH_2)_bSO_3H$, wherein a=0-2 and b=1-3;

$R_2$ and $R_3$ are independently H, or linear or branched $C_{1-20}$ alkyl;

$R_5$ and $R_6$, are independently H, F, Cl, Br;

R7 is H, or linear or branched $C_{1-4}$ alkyl or acetate;

R8 and R9 are independently H, or linear or branched $C_{1-4}$ alkyl or acetate; and m=1-3; n=1-4; and o=1-4;

and pharmaceutically acceptable salts thereof. $R_5$, $R_6$, $R_7$, $R_8$ and $R_9$ may be H, m and n may be 1 and o may be 2. More particularly, $R_1$ and $R_4$ may be the same, and or $R_2$ and $R_3$ may be the same. $R_1$ and $R_4$ may be —$CH_2COOH$ and/or $R_2$ and $R_3$ may be —$CH_2CH_3$ or —$(CH_2)_{11}CH_3$.

In yet another embodiment, there is provided a ligand metal complex having the formula:

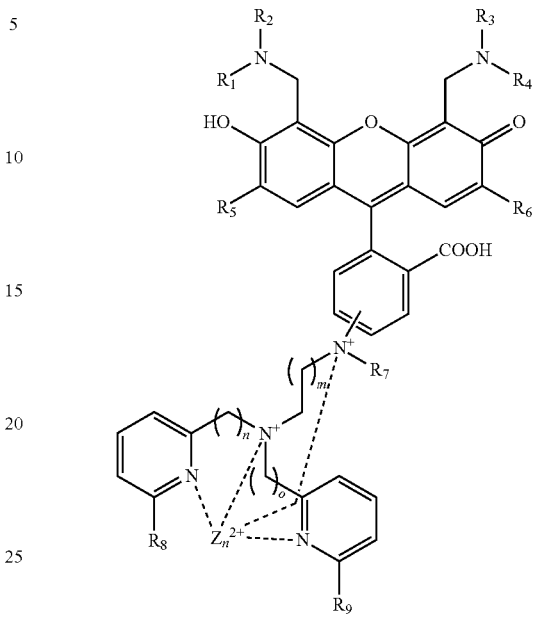

wherein $R_1$ and $R_4$ are independently H, or —$CH_2(CH_2)_aCOOH$, $CH_2(CH_2)_bSO_3H$, wherein a=0-2 and b=1-3;

$R_2$ and $R_3$ are independently H, or linear or branched $C_{1-20}$ alkyl;

$R_5$ and $R_6$ are independently H, F, Cl, Br;

R7 is H, or linear or branched $C_{1-4}$ alkyl or acetate;

R8 and R9 are independently H, or linear or branched $C_{1-4}$ alkyl or acetate; and m=1-3; n=1-4; and o=1-4;

and pharmaceutically acceptable salts thereof. $R_5$, $R_6$, $R_7$, $R_8$ and $R_9$ may be H, m and n may be 1 and o may be 2. More particularly, $R_1$ and $R_4$ may be the same, and or $R_2$ and $R_3$ may be the same. $R_1$ and $R_4$ may be —$CH_2COOH$ and/or $R_2$ and $R_3$ may be —$CH_2CH_3$ or —$(CH_2)_{11}CH_3$.

As used herein, the term "about" means within 10% of the stated value, or more preferentially within 5% of the value. As used herein the specification, "a" or "an" may mean one or more. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Chemical structure of ZIMIR in the $Zn^{2+}$-free (non-fluorescent) and $Zn^{2+}$-bound (strongly fluorescent) states. (FIG. 1B) Mode of action of ZIMIR for reporting local $Zn^{2+}$ elevation at the membrane surface during insulin release.

(FIG. 2B) NBS, BPO, $CCl_4$, reflux, 4 h, 98%; (reaction c) NaI, proton sponge, N-ethyl glycine methyl ester (for compound 3a), or N-dodecyl glycine ethyl ester (for compound 3b), $CH_3CN$, reflux, 14 hrs, 78-96%; (reaction d) NaHS, MeOH/THF/H2O (10/3/3), reflux, 1 h, 81% for 4a and 74% for 4b. (reaction e) 2-Bromo-1,1-dimethoxyethane, KF/celite (1:1), CH3CN, reflux, 3 days, 60%; (reaction f) 1 M HCl, 5 h, 99%; (reaction g) $NaBH_3CN$, $Na_2SO_4$, r.t., overnight, 36% for ZIMIR-C2; 18% for ZIMIR.

FIGS. 3A-D. (FIG. 3A) Absorption spectrum of ZIMIR-C2. (FIG. 3B) $Zn^{2+}$ dependent fluorescence enhancement of ZIMIR-C2. $Zn^{2+}$ concentrations (nM) were 0, 43, 140, 440, 840, 1640 and 6440 (from bottom to top). (FIG. 3C) $Zn^{2+}$ titration of ZIMIR-C2 as measured from its emission at 515 nm. The solid line represents the exponential fit. (FIG. 3D) ZIMIR-C2 binds $Zn^{2+}$ selectively against $Ca^{2+}$ (1 mM) and $Mg^{2+}$ (1 mM). All measurements were performed in buffers containing 100 mM Hepes, pH 7.5 with 0.4 μM of ZIMIR-C2.

(FIG. 5A) Example fluorescence images (Excitation 488±7.5 nm, emission 530±20 nm) of INS-1 cells labeled with ZIMIR at different $[Zn^{2+}]e$. (FIG. 5B) Quantification of the average ZIMIR fluorescence intensity along the plasma membrane (IZIMIR(PM)).

(FIGS. 6A-E) KCl stimulated insulin/$Zn^{2+}$ release in MIN6 cells. Example images of MIN6 cells (FIG. 6A, DIC/Normasky) before (FIG. 6B) and after KCl (40 mM, C) or $Zn^{2+}$ addition (1 μM, D). Time courses of ZIMIR signal changes (F/F0) in two example regions of interest (ROI, indicated in D by dashed lines) along the plasma membrane.

(FIG. 7A) Time courses of IZIMIR(PM) decay after washing INS-1 cells (initially bathed in FIBS containing 1 μM $Zn^{2+}$) with HBS containing EDTA (10 μM) and DPAS (0-8 μM). (FIG. 7B) ZIMIR imaging of insulin/$Zn^{2+}$ release of MIN6 cells bathed in SAB containing EDTA (10 μM) and DPAS (4 μM). Time courses of IZIMIR(PM) fluctuation of four separate regions of interest (ROI 1-4) and example ZIMIR images at different time points were shown (a-e; arrow heads highlighting local ZIMIR increases in separate ROIs at different time).

(FIGS. 8A-B) Confocal images of mouse islets labeled with ZIMIR (FIG. 8A) or calcein/AM (FIG. 8B). (FIG. 8C) Confocal ZIMIR imaging of insulin/$Zn^{2+}$ release in a mouse islet bathed in SAB. Images from two example layers 15 μm apart before and 10 sec post KCl (40 mM) stimulation were shown.

DESCRIPTION OF ILLUSTRATIVE EMBODIMENTS

Figure 1A:
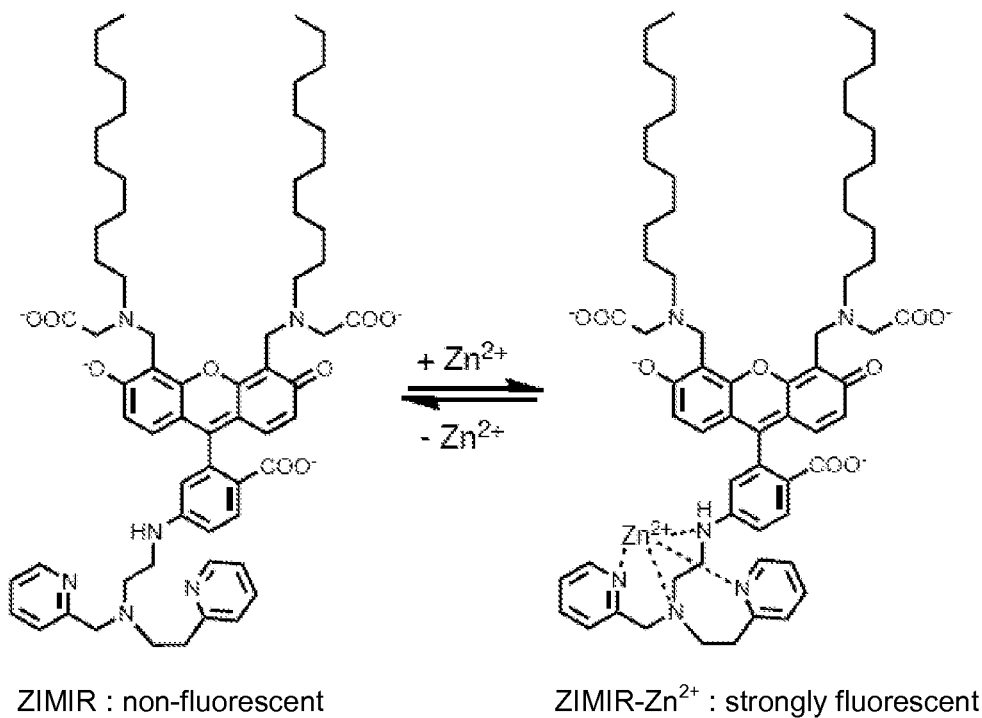
FIGS. 1A-B. Design of ZIMIR.
Figure 1B:
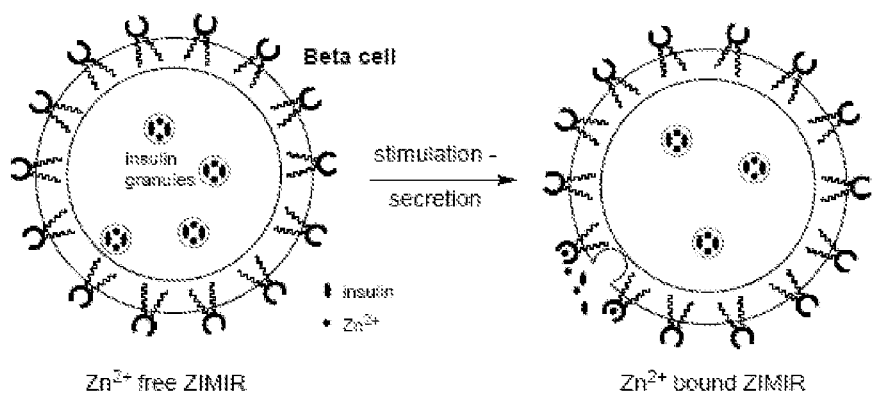

To follow the dynamics of excitation-secretion coupling (E-S coupling), and to monitor the release of these $Zn^{2+}$ containing granules in intact cells, the inventors have developed fluorescent $Zn^{2+}$ indicators that are specifically targeted to plasma membranes of cells. These membrane anchored $Zn^{2+}$ indicators (ZIMIR's), FIG. 1, abbreviated for Zinc Indicator for Monitoring Insulin Release, fluoresce very weakly in the absence of $Zn^{2+}$, but become strongly fluorescent when they bind to $Zn^{2+}$ during secretion (FIG. 1).

ZIMIR's are rapidly taken up by fully intact living cells. After staining, ZIMIR remains stably localized to plasma membranes so one can monitor it continuously over time to track cell secretion. During secretion, the elevation of $Zn^{2+}$ concentration ($[Zn^{2+}]$) would be highest immediately above the plasma membrane where ZIMIR is localized. Thus, the fluorescence signal of ZIMIR is highly sensitive to secretory activity—to an extent that it can even detect a highly localized and transient secretion event using digital fluorescence microscopy. Combined with fluorescence imaging modalities of high three dimensional selectivity such as confocal laser scanning microscopy (CLSM) or two photon laser scanning microscopy (2PLSM), ZIMIR offers the opportunity of tracking E-S coupling in cell populations with high spatiotemporal resolution.

In addition to cultured cells, ZIMIR also rapidly and non-invasively labels cells in tissues or in physiological preparations such as dissected pancreatic islets. Combined with CLSM and 2PLSM, ZIMIR offers the opportunity of monitoring secretory activity of cells in three dimensions in physiological preparations where normal cell-cell contacts are maintained.

This newly developed $Zn^{2+}$ sensor (ZIMIR) and fluorescence imaging assay offers major advantages over the imaging assays currently available for monitoring insulin release. Existing methods for imaging insulin release include $Zn^{2+}$ imaging using FluoZin-3; fluorescence imaging of fusion proteins consisting of green fluorescent protein (GFP) and insulin or C-peptide (Michael et al., 2007; Nagamatsu, 2006); and two photon extracellular polar tracer imaging (Kasai et al., 2005).

Applications of ZIMIR include (1) measuring secretory activity of cells that have $Zn^{2+}$ containing granules (e.g., pancreatic beta cells, submandibular salivary gland, the prostate epithelial cells, paneth cells in the crypts of Lieberkühn, mast cells, granulocytes, pituitary cells, and certain neurons of the central nervous systems), (2) investigating the regulation and mechanism of E-S coupling, (3) screening to identify lead compounds or genes that modulate (either enhance or inhibit) secretory activity of cells that have $Zn^{2+}$-containing granules, (4) characterizing insulin release activity of islet beta cells from healthy or diabetic subjects in greater detail in order to better understand how insulin secretion is altered in diabetes, and (5) facilitating tissue or cell engineering to select cells that maintain regulated and robust secretory activity (such cells may have a variety of applications, including, for example, cell therapy to treat type I diabetes by providing regulated insulin release in response to physiological demand).

This new class of $Zn^{2+}$ sensor possesses a number of salient features for monitoring dynamics of cell secretion: (1) non-invasive and rapid labeling of fully intact cell populations both in culture and in physiological preparations; (2) high sensitivity of detection and high spatial and temporal resolution when combined with CLSM or 2PLSM; (3) applicability to islets and beta cells isolated from rodents, other mammals, and primates including humans; (4) flexibility to be performed on a dozen cells or in a single islet, thus greatly reducing the amount of biological specimens required for performing an insulin assay as compared with the traditional techniques such as radioimmunoassay or ELISA; (5) single cell resolution and subcellular resolution of exocytosis, thus allowing examination of cell heterogeneity in E-S coupling; and (6) high temporal resolution, facilitating moment-to-moment correlation of intracellular signaling and exocytosis.

Other practical applications of this technique may include developing high throughput screenings to identify compounds or genes (by siRNA screening or by inhibiting miR-NAs) that regulate insulin secretion in beta cells. These compounds or genes may become lead targets for drug discovery. The imaging assays may also be applied to tissue engineering. For example, there is tremendous potential for using embryonic stem cells (ES cells) or induced pluripotent stem cells (iPS cells) to engineer insulin release beta cells for cell therapy against type I diabetes. This imaging assay can be applied to select ES cells or iPS cells that manifest robust glucose—(or any other secretagoges, either natural or synthetic) stimulated insulin release when these cells undergo differentiation in vitro. Single cell clones that maintain consistent insulin release activity will be selected, expanded and used for cell therapy.

These and other aspects of the invention are discussed in detail below.

I. Chemical Definitions

For the chemical groups described herein, the following parenthetical subscripts further define the groups as follows: "(Cn)" defines the exact number (n) of carbon atoms in the group. "(C≦n)" defines the maximum number (n) of carbon atoms that can be in the group, with the minimum number of carbon atoms in such at least one, but otherwise as small as possible for the group in question, e.g., it is understood that the minimum number of carbon atoms in the group "alkenyl$_{(C≦8)}$" is two. For example, "alkoxy$_{(C≦10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —$CH_3$ (Me), —$CH_2CH_3$ (Et), —$CH_2CH_2CH_3$ (n-Pr), —$CH(CH_3)_2$ (iso-Pr), —$CH(CH_2)_2$ (cyclopropyl), —$CH_2CH_2CH_2CH_3$ (n-Bu), —$CH(CH_3)$ $CH_2CH_3$ (sec-butyl), —$CH_2CH(CH_3)_2$ (iso-butyl), —$C(CH_3)_3$ (tert-butyl), —$CH_2C(CH_3)_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —$CH_2OH$, —$CH_2Cl$, —$CH_2Br$, —$CH_2SH$, —$CF_3$, —$CH_2CN$, —$CH_2C(O)H$, —$CH_2C(O)$ $OH$, —$CH_2C(O)OCH_3$, —$CH_2C(O)NH_2$, —$CH_2C(O)$ $NHCH_3$, —$CH_2C(O)CH_3$, —$CH_2OCH_3$, —$CH_2OCH_2CF_3$, —$CH_2OC(O)CH_3$, —$CH_2NH_2$, —$CH_2NHCH_3$, —$CH_2N$ $(CH_3)_2$, —$CH_2CH_2Cl$, —$CH_2CH_2OH$, —$CH_2CF_3$, —$CH_2CH_2OC(O)CH_3$, —$CH_2CH_2NHCO_2C(CH_3)_3$, and —$CH_2Si(CH_3)_3$.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2] oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide.

Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002).

II. Zinc Ion Release by Cells

Excitation-secretion coupling is an important aspect of cell signaling. It is nowhere more important than in the action of beta cells, which are a type of cell in the pancreas in areas called the islets of Langerhans. They make up 65-80% of the cells in the islets. Their release of zinc ions is closely tied to the packaging and release of insulin, and thus by measuring zinc release, the insulin-secreting function of islets cells also can be monitored.

Similarly, the application of this screening strategy can be applied to examine other secretory cells with granules that are enriched in $Zn^{2+}$, including the submandibular salivary gland (Frederickson et al., 1987), the prostate epithelial cells (Sorensen et al., 1997), paneth cells in the crypts of Lieberkühn (Giblin et al., 2006; Muller and Geyer, 1969), mast cells (Gustafson, 1967; Ho et al., 2004), granulocytes (Goldberg et al., 1993; Ieshchenko et al., 1994), pituitary cells (Thorlacius-Ussing, 1987), and certain neurons of the central nervous systems (Birinyi et al., 2001; Haug, 1967). These cells also release $Zn^{2+}$ during secretion and thus may also be imaged and used to develop cell-based screening.

III. Cellular Imaging

As discussed above, the present invention provides for new and improved methods of imaging zinc-secreting cells. Four particular types of microscopy are well-suited for exploiting the use of ZIMIRs in cellular imaging—wide field fluorescence microscopy, total internal reflection fluorescence microscopy, confocal laser scanning microscopy of and two phone laser scanning microscopy.

A. Wide Field Fluorescence Microscopy Wide field fluorescence microscopy involves the use of any microscope where the image formation takes place by the optic without scanning. The lens directly forms an image, which can be projected on a camera or observed through the oculars. The light source usually is a mercury or xenon lamp, but can also be an LED or laser. Thin specimens that do not require confocal imaging may be advantageously imaged using conventional wide field method as they offer unsurpassed signal to noise.

B. Total Internal Reflection Fluorescence Microscopy

A total internal reflection fluorescence microscope (TIRFM) is a type of microscope with which a thin region of a specimen, usually less than 200 nm, can be observed. TIRFM was developed at the University of Michigan in the early 1980s. A TIRFM uses evanescent wave to selectively illuminate and excite fluorophores in a restricted region of the specimen immediately adjacent to the glass-water interface. The evanescent wave is generated only when the incident light is totally reflected at the glass-water interface. The evanescent electromagnetic field decays exponentially from the interface, and thus penetrates to a depth of only approximately 100 nm into the sample medium. Thus the TIRFM enables a selective visualization of surface regions such as the basal plasma membrane (which are about 7.5 nm thick) of cells as shown in the figure above. Note, however, that the region visualized is at least a few hundred nanometers wide, so the cytoplasmic zone immediately beneath the plasma membrane is necessarily visualized in addition to the plasma membrane during TIRF microscopy. The selective visualization of the plasma membrane renders the features and events on the plasma membrane in living cells with high axial resolution. TIRF can also be used to observe the fluorescence of a single molecule, making it an important tool of biophysics and quantitative biology.

C. Confocal Laser Scanning Microscopy

Confocal laser scanning microscopy (CLSM or LSCM) is a technique for obtaining high-resolution optical images with depth selectivity. The key feature of confocal microscopy is its ability to acquire in-focus images from selected depths, a process known as optical sectioning. Images are acquired point-by-point and reconstructed with a computer, allowing three-dimensional reconstructions of topologically-complex objects. For opaque specimens, this is useful for surface profiling, while for non-opaque specimens, interior structures can be imaged. For interior imaging, the quality of the image is greatly enhanced over simple microscopy because image information from multiple depths in the specimen is not superimposed. A conventional microscope "sees" as far into the specimen as the light can penetrate, while a confocal microscope only images one depth level at a time. In effect, the CLSM achieves a controlled and highly limited depth of focus.

In 1978, Thomas and Christoph Cremer designed a laser scanning process, which scans the three dimensional surface of an object point-by-point by means of a focused laser beam, and creates the over-all picture by electronic means similar to those used in scanning electron microscopes. This CSLM design combined the laser scanning method with the 3D detection of biological objects labeled with fluorescent markers for the first time. During the next decade, confocal fluorescence microscopy was developed into a fully mature technology, in particular by groups working at the University of Amsterdam and the European Molecular Biology Laboratory (EMBL) in Heidelberg and their industry partners.

In a confocal laser scanning microscope, a laser beam passes through a light source aperture and then is focused by an objective lens into a small (ideally diffraction limited) focal volume within or on the surface of a specimen. In biological applications especially, the specimen may be fluorescent. Scattered and reflected laser light as well as any fluorescent light from the illuminated spot is then re-collected by the objective lens. A beam splitter separates off some portion of the light into the detection apparatus, which in fluorescence confocal microscopy will also have a filter that selectively passes the fluorescent wavelengths while blocking the original excitation wavelength. After passing a pinhole, the light intensity is detected by a photodetection device (usually a photomultiplier tube (PMT) or avalanche photodiode), transforming the light signal into an electrical one that is recorded by a computer.

The detector aperture obstructs the light that is not coming from the focal point, as shown by the dotted gray line in the image. The out-of-focus light is suppressed: most of the returning light is blocked by the pinhole, which results in sharper images than those from conventional fluorescence microscopy techniques and permits one to obtain images of planes at various depths within the sample (sets of such images are also known as "z stacks").

The detected light originating from an illuminated volume element within the specimen represents one pixel in the resulting image. As the laser scans over the plane of interest, a whole image is obtained pixel-by-pixel and line-by-line, whereas the brightness of a resulting image pixel corresponds to the relative intensity of detected light. The beam is scanned across the sample in the horizontal plane by using one or more (servo controlled) oscillating mirrors. This scanning method usually has a low reaction latency and the scan speed can be varied. Slower scans provide a better signal-to-noise ratio, resulting in better contrast and higher resolution. Information can be collected from different focal planes by raising or lowering the microscope stage or objective lens. The computer can generate a three-dimensional picture of a specimen by assembling a stack of these two-dimensional images from successive focal planes.

Confocal microscopy provides the capacity for direct, non-invasive, serial optical sectioning of intact, thick, living specimens with a minimum of sample preparation as well as a marginal improvement in lateral resolution. Biological samples are often treated with fluorescent dyes to make selected objects visible. However, the actual dye concentration can be low to minimize the disturbance of biological systems: some instruments can track single fluorescent molecules. Also, transgenic techniques can create organisms that produce their own fluorescent chimeric molecules (such as a fusion of GFP, green fluorescent protein with the protein of interest).

CLSM is a scanning imaging technique in which the resolution obtained is best explained by comparing it with another scanning technique like that of the scanning electron microscope (SEM). CLSM has the advantage of not requiring a probe to be suspended nanometers from the surface, as in an AFM or STM, for example, where the image is obtained by scanning with a fine tip over a surface. The distance from the objective lens to the surface (called the "working distance") is typically comparable to that of a conventional optical microscope. It varies with the system optical design, but working distances from hundreds of microns to several millimeters are typical.

In CLSM a specimen is illuminated by a point laser source, and each volume element is associated with a discrete scattering or fluorescence intensity. Here, the size of the scanning volume is determined by the spot size (close to diffraction limit) of the optical system because the image of the scanning laser is not an infinitely small point but a three-dimensional diffraction pattern. The size of this diffraction pattern and the focal volume it defines is controlled by the numerical aperture of the system's objective lens and the wavelength of the laser used. This can be seen as the classical resolution limit of conventional optical microscopes using wide-field illumination. However, with confocal microscopy it is even possible to improve on the resolution limit of wide-field illumination techniques because the confocal aperture can be closed down to eliminate higher orders of the diffraction pattern. For example, if the pinhole diameter is set to 1 Airy unit then only the first order of the diffraction pattern makes it through the aperture to the detector while the higher orders are blocked, thus improving resolution at the cost of a slight decrease in brightness. In fluorescence observations, the resolution limit of confocal microscopy is often limited by the signal to noise ratio caused by the small number of photons typically available in fluorescence microscopy. One can compensate for this effect by using more sensitive photodetectors or by increasing the intensity of the illuminating laser point source. Increasing the intensity of illumination later risks excessive bleaching or other damage to the specimen of interest, especially for experiments in which comparison of fluorescence brightness is required. When imaging tissues which are differentially refractive, such as the spongy mesophyll of plant leaves or other air-space containing tissues, spherical aberrations that impair confocal image quality are often pronounced. Such aberrations however, can be significantly reduced by mounting samples in optically transparent, non-toxic perfluorocarbons such as perfluorodecalin, which readily infiltrates tissues and has a refractive index almost identical to that of water.

D. Two Photon Laser Scanning Microscopy

Two-photon excitation microscopy is a fluorescence imaging technique that allows imaging of living tissue up to a very high depth, that is up to about one millimeter. Being a special variant of the multiphoton fluorescence microscope it uses red-shifted excitation light which can also excite fluorescent dyes however for each excitation two photons of the infrared light are absorbed. Using infrared light minimizes scattering in the tissue. Due to the multiphoton absorption background signal is strongly suppressed. Both effects lead to the increased penetration depth for these microscopes. However, the resolution remains diffracton-limited. Two-photon excitation can be a superior alternative to confocal microscopy due to its deeper tissue penetration, efficient light detection and reduced phototoxicity.

The concept of two-photon excitation is based on the idea that two photons of comparably lower energy than needed for one photon excitation can also excite a fluorophore in one quantum event. Each photon carries approximately half the energy necessary to excite the molecule. An excitation results in the subsequent emission of a fluorescence photon, typically at a higher energy than either of the two excitatory photons. The probability of the near-simultaneous absorption of two photons is extremely low. Therefore a high flux of excitation photons is typically required, usually a femtosecond laser.

The most commonly used fluorophores have excitation spectra in the 400-500 nm range, whereas the laser used to excite the two-photon fluorescence lies in the ~700-1000 nm (infrared) range. If the fluorophore absorbs two infrared photons simultaneously, it will absorb enough energy to be raised into the excited state. The fluorophore will then emit a single photon with a wavelength that depends on the type of fluorophore used (typically in the visible spectrum). Because two photons are absorbed during the excitation of the fluorophore, the probability for fluorescent emission from the fluorophores increases quadratically with the excitation intensity. Therefore, much more two-photon fluorescence is generated where the laser beam is tightly focused than where it is more diffuse. Effectively, excitation is restricted to the tiny focal volume (~1 femtoliter), resulting in a high degree of rejection of out-of-focus objects. This localization of excitation is the key advantage compared to single-photon excitation microscopes, which need to employ additional elements such as pinholes to reject out-of-focus fluorescence. The fluorescence from the sample is then collected by a high-sensitivity detector, such as a photomultiplier tube. This observed light intensity becomes one pixel in the eventual image; the focal point is scanned throughout a desired region of the sample to form all the pixels of the image.

In two-photon excitation microscopy, an infrared laser beam is focused through an objective lens. The Ti-sapphire laser normally used has a pulse width of approximately 100 femtoseconds and a repetition rate of about 80 MHz, allowing the high photon density and flux required for two photons absorption and is tunable across a wide range of wavelengths.

The use of infrared light to excite fluorophores in light-scattering tissue has added benefits. Longer wavelengths are scattered to a lesser degree than shorter ones, which is a benefit to high-resolution imaging. In addition, these lower-energy photons are less likely to cause damage outside the focal volume. Compared to a confocal microscope, photon detection is much more effective since even scattered photons contribute to the usable signal. There are several caveats to using two-photon microscopy: The pulsed lasers needed for two-photon excitation are much more expensive then the constant wave (CW) lasers used in confocal microscopy. The two-photon absorption spectrum of a molecule may vary significantly from its one-photon counterpart. For very thin objects such as isolated cells, single-photon (confocal) microscopes can produce images with higher optical resolution due to their shorter excitation wavelengths. In scattering tissue, on the other hand, the superior optical sectioning and light detection capabilities of the two-photon microscope result in better performance.

IV. Cell Staining

In certain embodiments, it may prove useful to counterstain cells with other agents, such as those that identify cell surface markers, or internal structures such as DNA, RNA, mitochondia, etc. Stains, marker agents or antibodies directed to these surface molecules can not only permit cell boundary identification, but can facilitate characterization of a cell being of a certain type, such as diseased (e.g., cancerous), or of a certain type, e.g., vasculature versus muscle.

A non-limiting list of dyes include nucleic acid dyes such as acridine orange, 7-aminoactinomycin D, ethidium bromide, ethidium homodimer, LDS 751, propidium iodide, Syto 11, 12, 20, 22, 16, Syto 14, 15, 25, Syto 17, 59, 61, Sytox green, thiazole blue, thiazole orange, ToPro 1, ToPro3; antibody labeling dyes for cell surface, cytoplasmic and nuclear antigens such as Alexa 488, APC, BODIPY FL, BODIPY 630/650, CY5, CY5.5, ECD, FITC, cytokeratin, hematoxylin-eosin, fluorescein-conjugated lectin, *Ulex europaeus* I (F-UEAI) counterstained with Harris hematoxylin, periodic acid-Schiff (PAS), bromodeoxyuridine, cathepsin B, Texas Red, rhodamine, cyanine, phycoerythrin, phycocyanin, allophycocyanin, o-phthaldehyde, fluorescamine, oregon green 488, PE, PE-APC, PE-Cy5, PerCP, PE-TR, rhodamine green and rhodol green; cell metabolism dyes such as BCECF, calcium green, carboxy-DCF, carboxy SNARF-1 AM, DilCn5, DiOCn3, Fluo-3, Fura Red, Green Fluorescent Protein, JC-1 and NBD-C6-Ceramide; UV dyes such as Hoechst and Dapi. Other stains are known in the art may be used, and are summarized in references such as Bedrossian (1998), herein incorporated by reference. The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

A fluorescent label with an excitation wavelength capable of being excited by the fluorescent emission of another fluorescent dye is contemplated.

The cell nucleus may be stained by specific stains, such as propidium iodide or sytox green. In a specific embodiment propidium iodide is used. The propidium iodide, in a specific embodiment, is excited by a 488 nm wavelength argon-ion laser, and the red fluorescence emission is measured by appropriate detector.

Differences between apical and basal surfaces may be determined. Topography (morphology) of a specific cell may be smooth, asymmetrical, symmetrical, uneven, or marked with small or large pocks. Extensions on cells such as filopodia may be visualized.

V. Cell Samples

As discussed above, while the present invention may be advantageously practiced on isolated cells, such as those in culture, it may also be used on tissue samples. Such samples can be achieved by any one of a variety of different means, largely depending on the nature of the sample to examined. For example, for examination of solid tissues, samples can be taken by biopsy which can be obtained through needle biopsy, endoscopy, laparoscopy, or cystoscopy. Alternatively, scrapings of cells can be taken from the tissue of interest.

Once obtained, it may be necessary to further process the samples before they are examined. Further processing may include various forms of physical arrangement of the samples. For example, with solid tissues, it may be necessary to prepare thin sections. It also may be desired to dissociate the cells from each other and disperse them as a thin film monolayer. Dissociation may be accomplished by physical or enzymatic means. Similarly, dissociated cells in fluid samples or in scrapings may be concentrated and dispersed in a monolayer. In other instances, it may be desirable to concentrate disperse cells as a pellet. This can be accomplished by centrifugation of the liquid samples. Further processing includes chemical treatments such as fixation steps. Exemplary treatments include alcohol fixation. Suitable alcohols include methanol, ethanol, propanol, isopropanol, n-butanol and t-butanol. Microscopic slides, typically glass or quartz, may be prepared using the concentrated or processed specimen to optimize cellular content.

VI. Kits

Any of the compounds or compositions described herein may be comprised in a kit. The kits will thus comprise, in suitable container means, compounds of the present invention, alternatively also include fluorescent dyes, antibodies, secondary antibodies, buffers and washes.

The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the fluorophore and antibodies, additional agent, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the fluorophore and antibodies are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

VII. Examples

The following example is included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods $Zn^{2+}$ titration and ion selectivity of ZIMIR. To measure the $Zn^{2+}$ affinity of ZIMIR, we performed Zn2+ titration of ZIMIR-C2 (0.4 µM) using a $Zn^{2+}$ buffering system based on nitrilotriacetic acid (NTA) (Komatsu et al., 2005). The buffer contained 100 mM HEPES (pH 7.5), 10 mM NTA and varying concentrations of $ZnSO_4$ (0-9 mM) to reach free Zn2+ concentration between 0.1 nM to 43 nM. $Zn^{2+}$ concentrations above 43 nM were not buffered. However, since the commercial Hepes always contains a trace amount of divalent metal ($\leqq 5$ ppm), it was necessary to add a minimum amount of NTA to chelate the residual $Zn^{2+}$ present in the Hepes solution. The inventors found that adding ~0.5 µM of NTA to 100 mM Hepes solution was sufficient to reduce the fluorescence of ZIMIR-C2 to the same level as seen in 43 nM (buffered) of free $Zn^{2+}$. From that point, increasing amount of $ZnSO_4$ was added to reach higher $Zn^{2+}$ concentrations. Two independent $Zn^{2+}$ titrations provided $Kd(Zn^2)$ values of 433 nM and 467 nM, with an average $Kd(Zn^{2+})$ of 450 nM. To examine the $Zn^{2+}$ binding selectivity of ZIMIR against $Ca^{2+}$ or $Mg^{2+}$, we measured the fluorescence intensity of ZIMIR-C2 in a nominally $Zn^{2+}$ free solution containing 50 µM DPAS or in a solution containing 1 µM ZnCl2, with or without $Ca^{2+}/Mg^{2+}$ (1 mM).

Cell culture and ZIMIR imaging by wide field fluorescence microscopy. Details of cell culture are described below. For cell imaging, we cultured cells in 35 mm petri dishes with glass-bottoms (MatTek, Ashland, Mass.). To label cells with ZIMIR, cells were washed with a Secretion Assay Buffer (SAB) containing 114 mM NaCl, 4.7 mM KCl, 1.2 mM $KH_2PO_4$, 2.5 mM $CaCl_2$, 1.16 mM $MgSO_4$, 3 mM glucose, and 20 mM HEPES (pH 7.4). The DMSO stock solution of ZIMIR. (1-2 mM) diluted in a small volume of SAB was added to cells to a final concentration of 1 µM. Cells were then incubated at ~25° C. for 20 min and washed with SAB before imaging. To image insulin/$Zn^{2+}$ secretion, we routinely included 10 µM of EDTA in SAB to chelate the residual $Zn^{2+}$ and to reduce the baseline fluorescence. In addition, DPAS (2-4 µM) was added to SAB in some experiments to better resolve the dynamics of oscillatory insulin release.

Membrane ZIMIR fluorescence intensity was measured by drawing regions of interest (ROIs) along the plasma membrane, and its time course was normalized against its baseline value after background subtraction, i.e., (F-Fbkg)/(F0-Fbkg), where Fbkg is the average background fluorescence intensity of a nearby area containing no cells. To image cellular $Ca^{2+}$ activity ([$Ca^{2+}$]c) and $Zn^{2+}$ release concurrently, the inventors loaded cells with both ZIMIR and Fura-2/AM (2 µM from 2 mM stock in DMSO) in the presence of pluronic F-127 (10% in DMSO) (Dakin and Li, 2007). During loading, DMSO was kept below 0.5% and Pluronic F-127 was less than 0.05%. Wide field fluorescence microscopy was carried out on inverted fluorescence microscopes as described (Guo et al., 2008).

Islets labeling and ZIMIR imaging by confocal laser scanning microscopy. Experiments with rodent animals were carried out according to protocols approved by the Institutional Animal Care and Use Committee of University of Texas Southwestern Medical Center. Rodent islets were isolated from Sprague-Dawley rats or C57BL/6 mice after digesting exocrine tissues of pancreas using collagenase as described below. To image insulin release in islets, the inventors labeled islets with ZIMIR (final concentration 2 µM with 0.025% Pluronic) in SAB buffer for 20 min. Labeled islets were then transferred to an imaging dish that had been coated with 0.5% PuraMatrix peptide hydrogel (BD Biosciences, Cat # 354250). Islets adhered to the PuraMatrix hydrogel within 5 min. They then imaged ZIMIR fluorescence by confocal laser scanning microscopy using a LSM510 imaging system (Carl Zeiss) and a 40× oil immersion objective (Dakin and Li, 2007).

Cell culture and dissociation of pancreatic islets. All the culture mediums contained penicillin (100 ti/mL) and streptomycin (100 U/mL). INS-1 cells were cultured in RPMI-1640 medium (Gibco, with 11.1 mM glucose) supplemented with 10% fetal bovine serum, 2-mercaptoethanol (50 µM), sodium pyruvate (1 mM), L-glutamine (2 mM) and HEPES (10 mM). MIN6 cells were cultured in high glucose DMEM medium (Gibco) containing 10% heat inactivated fetal bovine serum, 2-mercaptoethanol (3.5 µL for 1 L medium). Cells were grown in 5% $CO_2$ at 37° C. and passed by trypsinization when they reached >80% confluence. The culture medium was changed every 2-3 days.

Primary beta cells were prepared from dispersed islets. The inventors typically incubated ~100-500 islets in 1 mL accutase solution (Innovative Cell Technologies, catalogue number AT-104) for 15 minutes at 37° C. and gently pipetted cells up and down for 15-20 times to promote dissociation. Digestion was stopped by adding 9 mL culture medium and cells were collected by centrifugation at 1300 rpm for 5 minutes. Dissociated islet cells were then resuspended in the culture medium and seeded in imaging dishes. Rodent islet cells were cultured in RPMI-1640 supplemented with 10% heat inactivated FBS. Human islet cells were cultured in CMRL medium (Mediatech, Inc) supplemented with 10% FBS and glucose (final concentration 10 mM).

ZIMIR imaging by wide field fluorescence microscopy. Wide field fluorescence microscopy was carried out on an inverted fluorescence microscope (Axiovert 200, Carl Zeiss) equipped with a cooled CCD camera (ORCA-ER, Hamamatsu). Cells were excited with light from a 175 W xenon lamp after passing through appropriate bandpath filters (Dakin and Li, 2007) and a 40× objective. Hardware automation, image acquisition and image analysis were carried out with the Openlab imaging software (Perkin Elmer).

To characterize the response of membrane anchored ZIMIR to changes of extracellular $Zn^{2+}$ concentration ([$Zn^{2+}$]), the inventors varied [$Zn^{2+}$]e from low nanomolar to micromolar, using $Zn^{2-1}$ buffers containing nitrilotriacetic acid (for [$Zn^{2+}$]e<100 nM) (Hirano et al., 2000) or histidine (for [$Zn^{2+}$]e. 100 nM) (Hauser and Tsien, 2007). After recording fluorescence images at different [$Zn^{2+}$]e levels, the inventors washed cells with a nominally $Zn^{2+}$ free SAB containing 0.2 mM DPAS and followed the decay of $I_{ZIMIR(PM)}$.

Islets isolation and preparation of primary beta cells from dissected islets. Rodent islets were isolated from Sprague-Dawley rats or C57BL/6 mice after digesting exocrine tissues of pancreas using collagenase (Li et al., 2009). Briefly, young adult animals 12-20 weeks old were anesthetized by intraperitoneal injection of nembutal and sacrificed by cervical dislocation. The internal organs were exposed after abdominal incision. After clamping the ampulla on the duodenum wall, the inventors perfused the pancreas with ~4 mL of collagenase solution (Roche Collagenase P, cat. #11213857001; 1.4 mg/mL dissolved in Hanks Balanced Salt Solution). The pancreas was then digested in another 1 mL collagenase solution at 37° C. for ~15 min. When the digestion suspension became homogenous and appeared milky, the inventors stopped the digestion by leaving the tube on ice and adding 14 mL of cold HBSS. Cells were centrifuged at 250 g for 2 min. Supernatant was decanted and cells were resuspend in 10 mL HBSS. After repeating the process one more time, the inventors hand-picked the resuspended islets using a pipette under a dissection scope. Isolated rodent islets were cultured at 37° C. with 5% $CO_2$ in RPMI 1640 medium containing 10% PBS.

Human islets were obtained through the Integrated Islet Distribution Program (IIDP) sponsored by the National Institute of Diabetes and Digestive and Kidney Diseases (NIDDK) and the Juvenile Diabetes Research Foundation International (JDRFI). Human islets were cultured at low density (1000 islet equivalents/mL) in CMRL medium (Mediatech, Inc) supplemented with 10% FBS and glucose (final concentration 10 mM) at in 5% $CO_2$. Upon receiving human islets, the inventors first incubated them at 37° C. overnight before culturing them at 25° C.

Synthesis. All reagents were purchased from Aldrich or VWR. Anhydrous solvents were stored over activated molecular sieves (3 Å or 4 Å). Thin layer chromatography (TLC) was performed on precoated silica gel 60F-254 glass plates (EM Science). Reaction products were purified by low pressure flash chromatography (FC) using silica gel 60 (63-200 μm, EM Science). $^1$H-NMR spectra were acquired on Varian 400 MHz or 500 MHz spectrometers. Chemical shifts (6, ppm) were reported against tetramethylsilane (0 ppm). MALDI-TOF mass spectrometry was performed on a Voyager-DE PRO biospectrometry workstation (Applied Biosystems) using 2,5-dihydroxy benzoic acid as the matrix.

2-[Bis(2-pyridinylmethyl)amino]-ethanesulfonic acid (dipicolylamine N-ethylsulfonate or DPAS) (Liang et al., 2005), 2-pyridylmethyl-[2-(2-pyridyl)ethyl]amine (compound 5) (Komatsu et al., 2005), and N-ethyl glycine methyl ester or N-dodecyl glycine ethyl ester (Neuschl et al., 2007) were prepared according to the published procedures.

Preparation of 6-nitro-4',5'-dimethylfluorescein dipivaloyl ester (compound 1). 4-Nitrophthalic acid anhydride (0.97 g, 5.0 mmol) and 2-methyl resorcinol (1.30 g, 10.5 mmol) were suspended in 100 mL of methanesulfonic acid. The mixture was stirred at 80° C. for 8 hours. After cooling, the reaction was quenched in 100 mL of ice water, and the mixture was passed through a sintered glass filter. The retentate was dried under vacuum at 50° C. for 8 hrs. The resulting dark red solid was then added to a suspension of $Cs_2CO_3$ (3.58 g, 11 mmol) in DMF (20 mL). To this solution was added 2.24 mL of pivalic anhydride. Two h later, the reaction mixture was filtered and the residue was washed with MeOH (20 mL). The filtrate was evaporated and the resulting residue was extracted with CHCl3 (3×50 mL) and saturated brine.

The organic layer was dried over Na2SO4, concentrated, and purified by FC (hexane/EtOAc, 20:1-4:1) to provide the product (5-nitro isomer, 0.607 g, 21.2%), the 6-nitro isomer (0.780 g, 27.2%) and the mixture of both isomers (1.338 g, 46.7%) as white solids.

5-Nitro-4',5'-dimethylfluorescein dipivaloyl ester: 1H NMR (CDCl$_3$, 400 MHz): δ 8.86 (d, J=2.0 Hz, 1H), 8.52 (dd, J=2.0, 8.4 Hz, 1H), 7.37 (d, J=8.4 Hz, 1H), 6.76 (d, J=8.8 Hz, 2H), 6.64 (d, J=8.8 Hz, 2H), 2.34 (s, 6H), 1.40 (s, 18H). MS: 573.20 calcd. for $C_{32}H_{31}NO_9$; obsd: 574.57 (M+H)+, 596.52 (M+Na)+.

6-Nitro-4',5'-dimethylfluorescein dipivaloyl ester (1): 1H NMR (CDCl$_3$, 400 MHz): δ 8.47 (dd, J=2.0, 8.4 Hz, 1H), 8.20 (d, J=8.4 Hz, 1H), 8.00 (d, J=2.0 Hz, 1H), 6.76 (d, J=8.8 Hz, 2H), 6.65 (d, J=8.8 Hz, 2H), 2.35 (s, 6H), 1.40 (s, 18H). MS: 573.20 calcd. for $C_{32}H_{31}NO_9$; obsd: 574.57 (M+H)+, 596.52 (M+Na)+.

Preparation of 6-nitro-4',5'-dibromomethylfluorescein dipivaloyl ester (compound 2). Compound 1 (57.4 mg, 0.10 mmol) mixed with N-bromosuccinimide (55.2 mg, 0.31 mmol) and benzoyl peroxide (10 mg) in $CCl_4$ (10 mL) was refluxed for 4 h. The mixture was cooled and filtered, and the solid residue was washed with $Et_2O$. The filtrate was concentrated and purified by FC (hexane/EtOAc, 10:1-8:1) to afford 2 (72 mg, 98.4%). 1H NMR (CDCl$_3$, 400 MHz): δ 8.52 (dd, J=2.0, 8.4 Hz, 1H), 8.24 (d, J=8.4 Hz, 1H), 8.07 (d, J=2.0 Hz, 1H), 6.93 (d, J=8.8 Hz, 2H), 6.80 (d, J=8.8 Hz, 2H), 4.80 (d, J=2.4 Hz, 4H), 1.44 (s, 18H). MS: 731.02 calcd. for $C_{32}H_{29}Br_2NO_9$; obsd: 732.35 (M+H)+.

Preparation of 2,2-Dimethoxy-N-[2-(2-pyridinyl)ethyl]-N-(2-pyridinylmethyl)-aminoethane (6 & 7). These compounds were prepared based on a known procedure (hang et al., 2008). Compound 5 (0.646 g, 3.03 mmol) (Komatsu et al., 2005) was mixed with 2-bromo-1,1-dimethoxyethane (1.44 mL, 12.12 mmol), $Na_2CO_3$ (3.21 g, 30.3 mmol) and KF/celite (1/1, 240 mg) in 18 mL of acetonitrile. The mixture was refluxed for 3 days under argon, cooled and filtered. The solid residue was washed with $CH_3CN$. The filtrate was concentrated and purified by FC (dichloromethane/MeOH, 50:1-20:1) to afford 6 (0.542 g, 59%) as a yellow oil. 1H NMR (CDCl$_3$, 400 MHz): δ 8.51 (m, 2H), 7.60 (qd, J=7.6, 2.0 Hz, 2H), 7.37 (d, J=7.6 Hz, 1H), 7.11 (m, 3H), 4.46 (t, J==5.2 Hz, 1H), 3.93 (s, 2H), 3.32 (s, 6H), 3.05 (4H, m), 2.80 (214, d, J=5.6 Hz). MS: 301.18 calcd. for $C_{17}H_{23}N_3O_2$; obsd: 302.46 (M+H)+.

The above intermediate 6 (0.344 g, 1.14 mmol) was suspended in an aqueous 1 N HCl solution (16 mL) and stirred at r.t. for 6 h. The solvent was removed under vacuum and the residue was dried under a high vacuum overnight to provide the product as a yellow solid (0.482 g). 1H NMR (D4-MeOH, 400 MHz): δ 8.95 (d, J=6.0 Hz, 1H), 8.67 (dd, J=6.0, 0.8 Hz, 1H), 8.05 (d, 8.4 Hz, 1H), 7.96 (t, J=6.8 Hz, 1H), 7.88 (m, 2H), 6.05 (t, J=4.4 Hz, 1H), 4.36 (s, 2H), 3.45-3.37 (m, 4H), 3.18 (m, 2H). MS: 256.14 calcd. for $C_{15}H_{18}N_3O+$; obsd: 256.34 M+.

Preparation of compound 3. A mixture of 2 (33.6 mg, 46 μmol), NaI (13.8 mg, 92 μmol), N-ethyl glycine methyl ester (184 μmol) and proton sponge (20 mg, 92 μmol) in anhydrous acetonitrile (1.0 mL) was fluxed overnight. The solution was concentrated and the residue was purified by FC (hexane/EtOAc, 20:1-2:1) to yield the product 3a as a yellow oil (96%). 1H NMR (CDCl$_3$, 400 MHz): δ 8.46 (dd, J=1.8, 8.4 Hz, 1H), 8.18 (d, J=8.4 Hz, 1H), 8.08 (d, J=1.8 Hz, 1H), 6.75 (s, 4H), 4.18 (m, 4H), 3.58 (s, 614), 3.47 (s, 4H), 2.84 (q, J=7.2 Hz, 4H), 1.37 (s, 18H), 1.02 (t, J=7.2 Hz, 6H).

Compound 3b was prepared similarly from 2 and N-dodecyl glycine ethyl ester in 78% yield. 1H NMR (CDCl$_3$, 400 MHz): δ 8.46 (dd, J=2.0, 8.4 Hz, 1H), 8.17 (d, J=8.4 Hz, 1H), 8.03 (d, J=2.0 Hz, 1H), 6.75 (s, 4H), 4.18 (m, 4H), 4.04 (m, 4H), 3.46 (s, 4H), 2.74 (t, J=7.4 Hz, 4H), 1.38 (s, 18H), 1.20 (m, 46H), 0.86 (t, J=7.4 Hz, 6H). MS: 1111.67 calcd. for C64H93N3O13; obsd: 1112.32 (M+H)+.

Preparation of compound 4. To a solution of compound 3a (84 μmol) in MeOH/THF/H2O (4/1/1, 6 mL) was added sodium hydrosulfide hydrate (400 mg, 68%). The mixture was refluxed for 1.5 h. The solvent was concentrated under vacuum and the residue was purified by reversed phase column chromatography (LiChroprep RP-18) to yield the product (4a) as a red solid (81%). 1H NMR (D4-MeOH, 400 MHz): δ 7.88 (d, J=8.4 Hz, 1H), 7.07 (d, 9.6 Hz, 2H), 6.80 (dd, J=2.4, 8.8 Hz, 1H), 6.51 (d, J=9.2 Hz, 2H), 6.41 (d, J=2.4 Hz, 1H), 4.01 (m, 2H), 3.85 (m, 2H), 3.18. 3.35 (m, 4H), 3.15-2.75 (m, 4H), 1.17 (t, J=7.2 Hz, 6H). MS: 577.21 calcd. for $C_{30}H_{31}N3O_9$; obsd: 578.16 (M+H)−.

Compound 4b was prepared similarly from compound 3b in 74% yield. 1H NMR (D4-MeOH, 400 MHz): δ 7.84 (d, J=8.8 Hz, 1H), 7.15 (d, J=9.2 Hz, 2H), 6.80 (dd, J=2.4, 8.4 Hz, 1H), 6.53 (d, J=9.2 Hz, 2H), 6.39 (d, J=2.4 Hz, 1H), 4.64 (m, 4H), 3.65 (m, 4H), 3.25 (m, 4H), 1.83 (m, 4H), 1.20-1.45 (m, 36H), 0.88 (m, 6H). MS: 857.52 calcd. for C50H71N3O9; obsd: 858.11 (M−H)+, 615.21 (M-$C_{14}H_{28}NO_2$)+, 372.22 (M-$C_{28}H_{57}N_2O_4$)+.

Preparation of ZIMIR-C2 and ZIMIR. The general procedure of preparing ZIMIRs involves mixing compound 4 with three equivalents of compound 7 in anhydrous MeOH containing dried $Na_2SO_4$ (100 eq.). The mixture was stirred at r.t. for several hours under argon. $NaCNBH_3$ (5 eq.) was then added. The reaction was continued overnight and the mixture was filtered. The filtrate was concentrated and the resulting residue was purified by reversed phase column chromatography (LiChroprep RP-18). ZIMIR-C2 was obtained as a red film in 36% yield. 1H NMR (D4-MeOH, 400 MHz): δ 8.33 (t, J=6.0 Hz, 2H), 7.86 (d, J=8.8 Hz, 1H), 7.63 (td, J=7.6, 2.0 Hz, 1H), 7.55 (td, J=7.6, 2.0 Hz, 1H), 7.21 (d, J=8.0 Hz, 2H), 7.16 (m, 2H), 7.09 (d, J=9.2 Hz, 2H), 6.66 (dd, J=2.4, 8.8 Hz, 1H), 6.50 (d, J=9.2 Hz, 2H), 6.20 (d, J=2.0 Hz, 1H), 4.73 (m, 4H), 3.78 (s, 2H), 3.68 (m, 4H), 3.35 (m, 4H), 3.11 (t, J=6.0 Hz, 2H), 2.91 (s, 4H), 2.75 (t, J=6.0 Hz, 2H), 1.40 (t, J=7.2 Hz, 61-1). MS: 816.35 calcd. for $C_{45}H_{48}N_6O_9$; obsd: 817.33 (M+H)+, 714.42 (M-$C_4H_8NO_2$)+, 611.47 (M$C_8H_{17}N_2O_4$)+, 520.45 (M-$C_{14}H_{22}N_3O_4$)+.

ZIMIR was obtained as a red film in 18% yield. 1H NMR (D4-MeOH, 400 MHz): δ 8.33 (m, 2H), 7.86 (d, J=8.4 Hz, 1H), 7.63 (td, J=7.6, 2.0 Hz, 1H), 7.55 (td, J=7.6, 2.0 Hz, 1H), 7.21-7.12 (m, 4H), 7.00 (d, J=9.2 Hz, 2H), 6.66 (dd, J=2.4, 8.8 Hz, 1H), 6.52 (d, J=9.2 Hz, 2H), 6.20 (d, 2.0 Hz, 1H), 4.63 (m, 4H), 3.78 (s, 2H), 3.65 (m, 4H), 3.35 (m, 4H), 3.11 (t, J=6.0 Hz, 2H), 2.90 (s, 4H), 2.68 (t, J=5.6 Hz, 2H), 1.84 (m, 4H), 1.38-1.10 (m, 36H), 0.88 (t, J=7.2 Hz, 6H). MS: 1096.66 calcd. for $C_{65}H_{88}N_6O_9$; obsd: 854.13 (M-$C_{14}H_{28}NO_2$)+, 611.19 (M$C_{28}H_{57}N_2O_4$)+, 520.24 (M-$C_{34}H_{62}N_3O_4$)+.

Example 2

Results

Design, syntheses and in vitro characterization of ZIMIR. To develop a robust imaging assay for monitoring insulin secretion and to boost the sensitivity of $Zn^{2+}$ detection near the plasma membrane, the inventors designed a membrane-anchored fluorescent $Zn^{2+}$ indicator, ZIMIR (Zinc Indicator for Monitoring Insulin Release, FIGS. 1A-B). ZIMIR consists of three moieties: a fluorophore based on fluorescein, a $Zn^{2+}$ binding motif derived from dipicolylamine (Komatsu et al., 2005), and a pair of dodecyl alkyl chains for membrane tethering. In the absence of $Zn^{2+}$, the fluorescence of ZIMIR is quenched by the photo-induced electron transfer from the amino group to fluorescein. When ZIMIR binds $Zn^{2+}$, the lone pair electrons of the nitrogen atom of 6-aminofluorescein coordinate around $Zn^{2+}$, resulting in the dequenching of ZIMIR fluorescence. At physiological pH, ZIMIR is an amiphiphilic molecule containing 4 negative charges, preventing its diffusion across hydrophobic cell membranes by itself. This restricts the probe to the outer leaflet of the lipid bilayer after the insertion of its two alkyl chains into the plasma membrane. During granule exocytosis and insulin secretion, the elevation of local $Zn^{2+}$ concentration([$Zn^{2+}$]) is expected to be highest immediately adjacent to the plasma membrane where ZIMIR is localized. Thus, the fluorescence readout of ZIMIR should be highly sensitive to beta cells' secretory activity.

Figure 2:
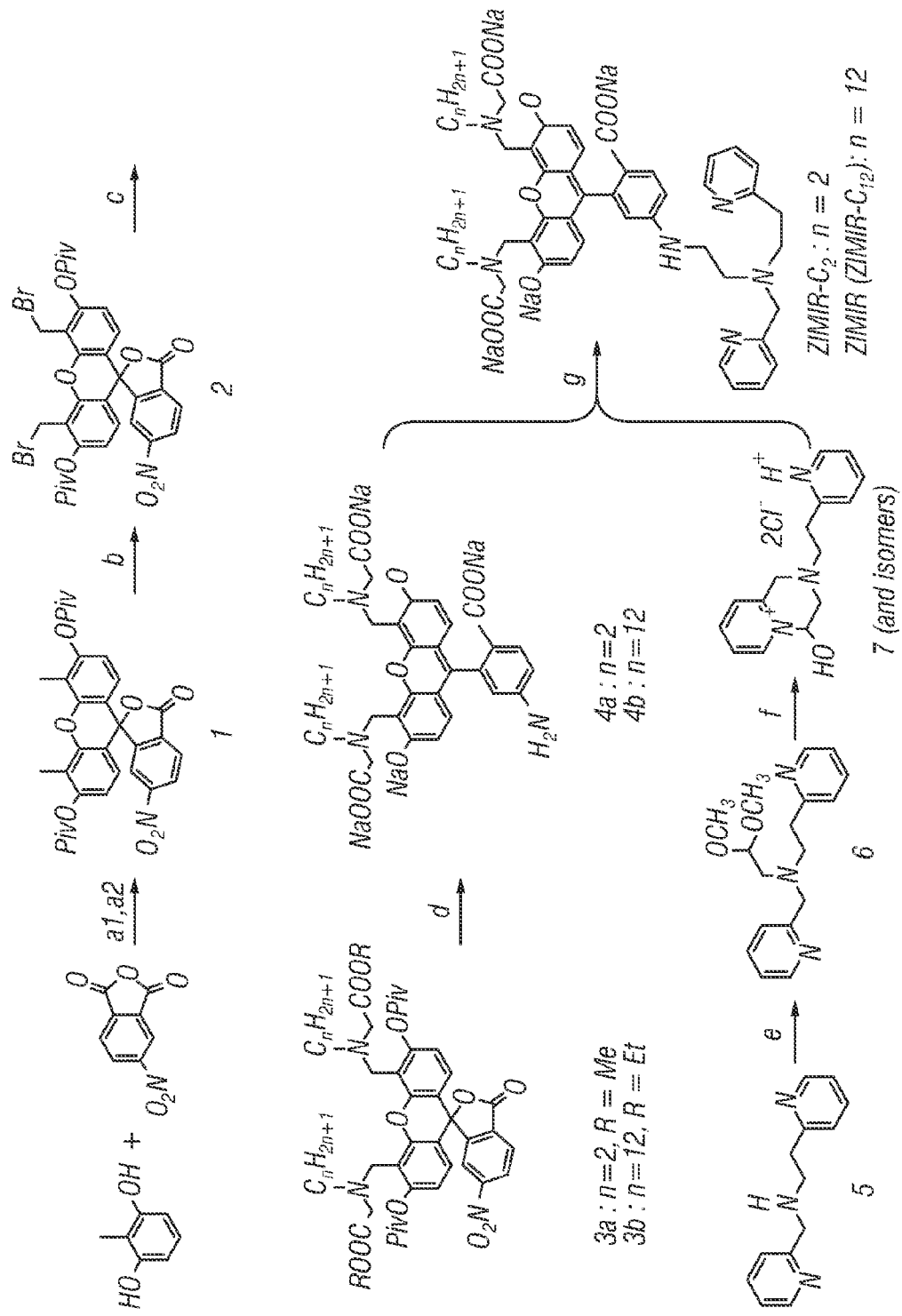
FIG. 2. Synthesis of ZIMIRs. (reaction a1) CH3SO3H, reflux, 8 hrs; reaction a2) Piv2O, $Cs_2CO_3$, DMF, r.t., 27% for 2 steps.

The inventors synthesized ZIMIR in a total of 8 steps (FIG. 2). To facilitate characterizing the fluorescent properties in aqueous solutions, the inventors also prepared a highly soluble ZIMIR homologue in which two dodecyl alkyl chains were replaced by a pair of ethyl groups (ZIMIR-C2, FIG. 2). The absorption maximum of ZIMIR-C2 centered around 493 nm with an extinction coefficient of 73,000 M-1 cm-1. At low nanomolar [$Zn^{2+}$], ZIMIR-C2 was nearly non-fluorescent (fluorescence quantum yield Qf (0 $Zn^{2+}$) =0.0032) (FIGS. 3A-D). Its fluorescence intensity increased with [$Zn^{2+}$]and reached a plateau at micromolar [$Zn^{2+}$], with an overall fluorescence enhancement of 70-fold upon $Zn^{2+}$ complexation (Qf ($Zn^{2+}$) =0.225), providing a $Zn^{2+}$ binding dissociation constant of 0.45 µM (FIG. 3C). To confirm that ZIMIR-C2 binds $Zn^{2+}$ selectively against interfering divalent cations present in physiological salines, the inventors measured its fluorescence in the presence of $Ca^{2+}$ and $Mg^{2+}$. At millimolar concentrations, neither $Ca^{2+}$ nor $Mg^{2+}$ affected ZIMIR-C2 fluorescence, nor did they affect [$Zn^{2+}$]-dependent fluorescence enhancement displayed by ZIMIR-C2 (FIG. 3D).

Figure 4C:
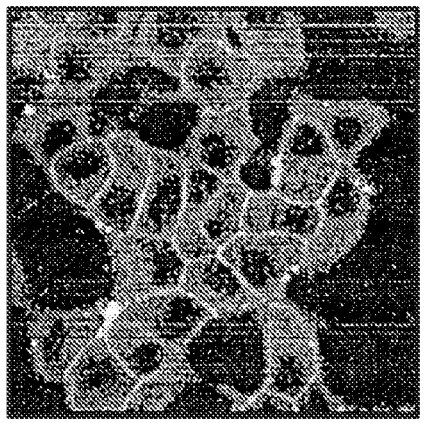
FIGS. 4A-F. ZIMIR labels plasma membranes of intact living cells rapidly, non-invasively and stably. ZIMIR (1 μM) was added to MIN6 cells in FIBS buffer (containing ~1 μM $Zn^{2+}$ enhance fluorescence intensity). Confocal images (Ex 488 nm, Em 510-550 nm) were subsequently acquired at 2 min (FIG. 4A), 5 min (FIG. 4B), 10 min (FIG. 4C), and 20 min (FIG. 4D). Cells were then washed with FIBS buffer three times and imaged again at 21 min (FIG. 4E), and 140 min (FIG. 4F).
Figure 4F:
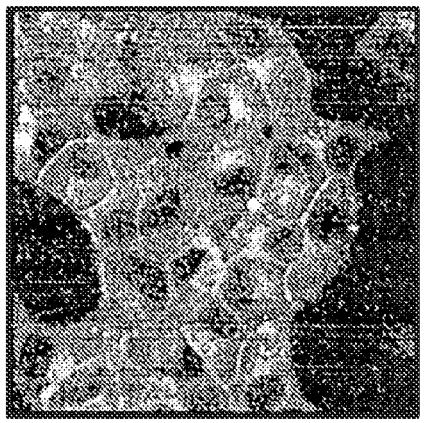
Figure 4B:
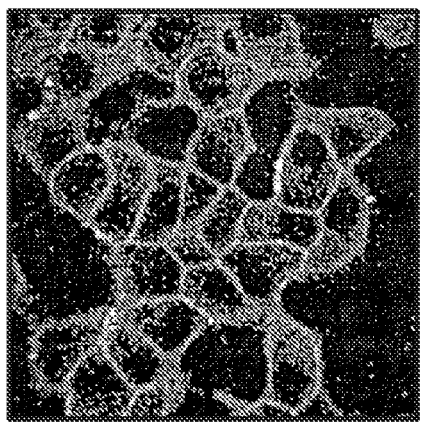
Figure 4E:
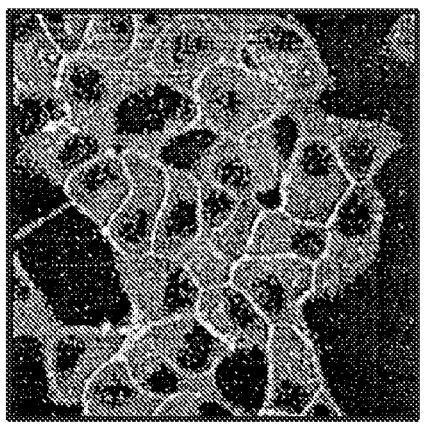
Figure 4A:
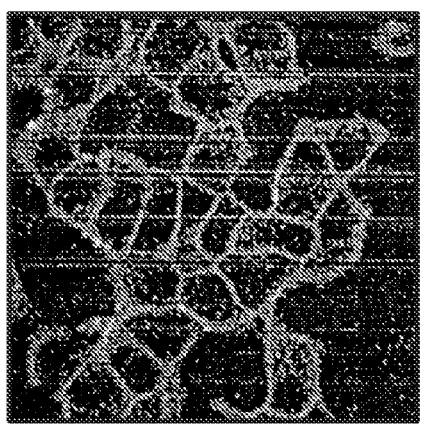
Figure 4D:
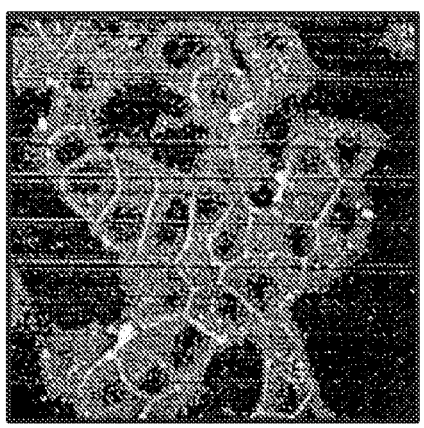

ZIMIR uptake and Zn2+ response in live cells. To examine the cellular uptake of ZIMIR, the inventors used a mouse insulinoma cell line, MIN6 (Miyazaki et al., 1990). When ZIMIR was incubated with cells at 1 µM concentration, it rapidly adhered to the cell surface of intact living cells (data not shown). In order to test the specificity and stability of membrane labeling, the inventors used confocal laser scanning microscopy (CLSM) to follow the cellular uptake and distribution of ZIMIR in MIN6 cells (FIGS. 4A-F). Within 5 min after probe addition, there was already a clear accumulation of ZIMIR along the plasma membrane (FIGS. 4A-B). By 20 min, the cellular uptake of ZIMIR appeared to reach completion (FIGS. 4C-D). Subsequent repetitive washings did not change membrane fluorescence intensity, suggesting strong association between ZIMIR and membrane lipids once ZIMIR was anchored to the plasma membrane (FIG. 4E). It is worth noting that another ZIMIR homologue containing a pair of nonyl alkyl chains, ZIMIR-C9, was also taken up by cells but failed to adhere to cell membranes upon washing (data not shown), suggesting that a minimum of two decyl chains is required for ZIMIRs to remain tightly associated with membrane lipids. Once taken up by cells, there was a gradual internalization of ZIMIR into the intracellular compartments, yet a sizable portion of ZIMIR still remained on the plasma membranes (FIG. 4F). The inventors routinely loaded cells with ZIMIR (0.5-1 µM) for ~20 min before washing and imaging. Further testing of ZIMIR in other beta cells including the rat insulinoma cell line INS-1 and primary beta cells isolated from mouse, rat or human islets, as well as in other types of cell lines such as Hela, HEK-293 and COS cells confirmed the same cellular uptake pattern and membrane labeling properties, suggesting its high efficiency of membrane labeling to be general among cultured mammalian cells. Moreover, cells labeled with ZIMIR showed the same growth rate as unlabeled cells over the next several days, suggesting that ZIMIR labeling caused very little cytotoxicity.

Figure 5A:
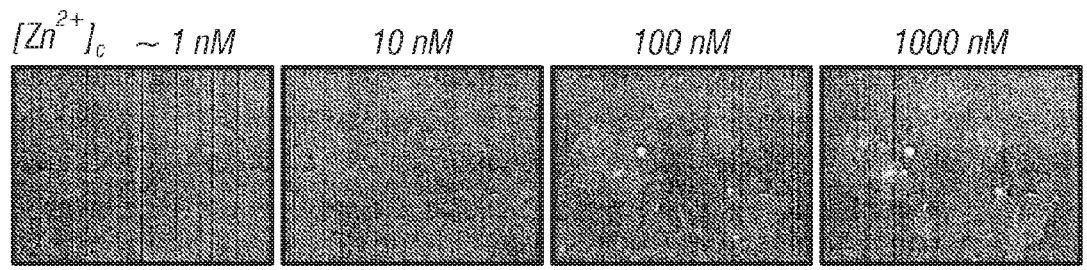
FIGS. 5A-B. Membrane anchored ZIMIR reports changes of $[Zn^{2+}]e$.
Figure 5B:
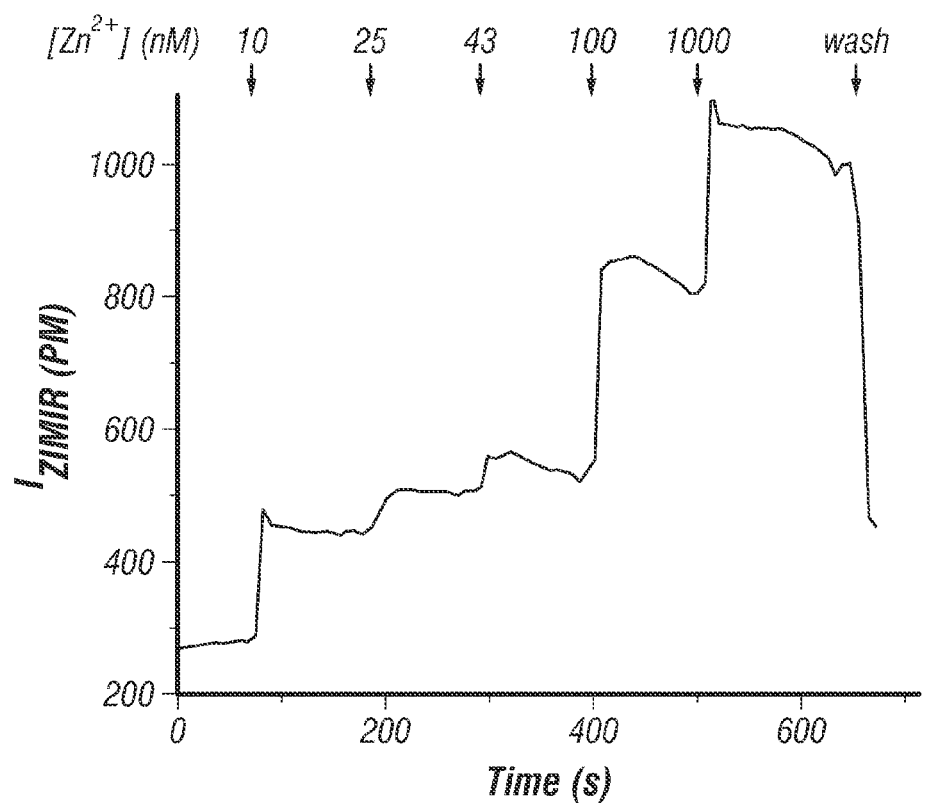

Membrane-anchored ZIMIR reliably reports fluctuations of [$Zn^{2+}$] in the extracellular medium. After labeling cells with ZIMIR, the inventors varied extracellular [$Zn^{2+}$]([$Zn^{2+}$]e) from nanomolar to micromolar levels. Intensity of ZIMIR fluorescence along the plasma membrane (IZIMIR(PM)) displayed a stepwise increase with incremental level of [$Zn^{2+}$]e (FIGS. 5A-B). After washing out $Zn^{2+}$, membrane ZIMIR intensity declined as expected from the reversibility of $Zn^{2+}$-binding.

Epifluorescence ZIMIR imaging of insulin/Zn2+ release. To image insulin/$Zn^{2+}$ secretion, the inventors used non-confocal (epifluorescence) microscopy and stimulated MIN6 cells with a high KCl concentration (40 mM) to depolarize the cell membrane and to activate the voltage operated $Ca^{2+}$ channels (VOCC). Subsequent $Ca^{2+}$ influxes triggered insulin release and, as expected, caused a robust enhancement in ZIMIR fluorescence (FIGS. 6A-E).

Figure 6A:
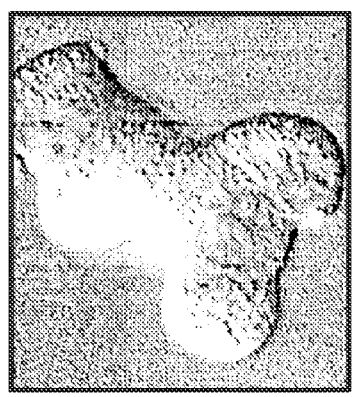
FIGS. 6A-E. ZIMIR imaging of insulin/$Zn^{2+}$ release.
Figure 6B:
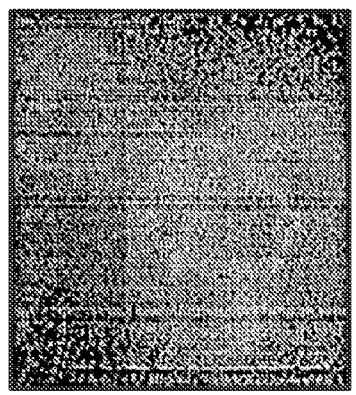
Figure 6C:
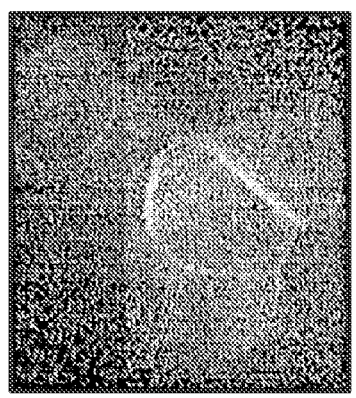
Figure 6D:
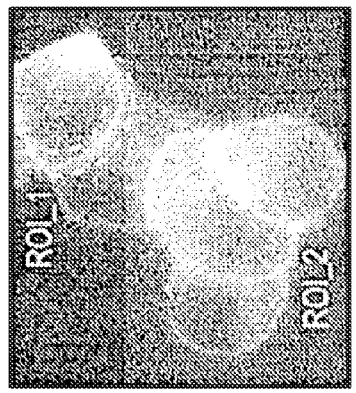
Figure 6E:
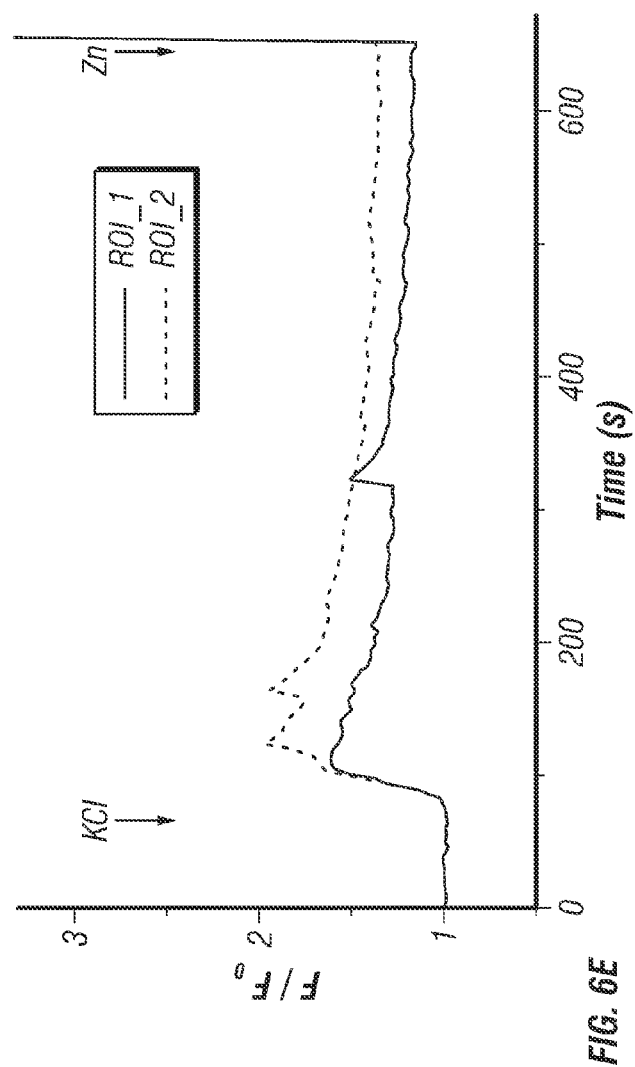
Figure 7A:
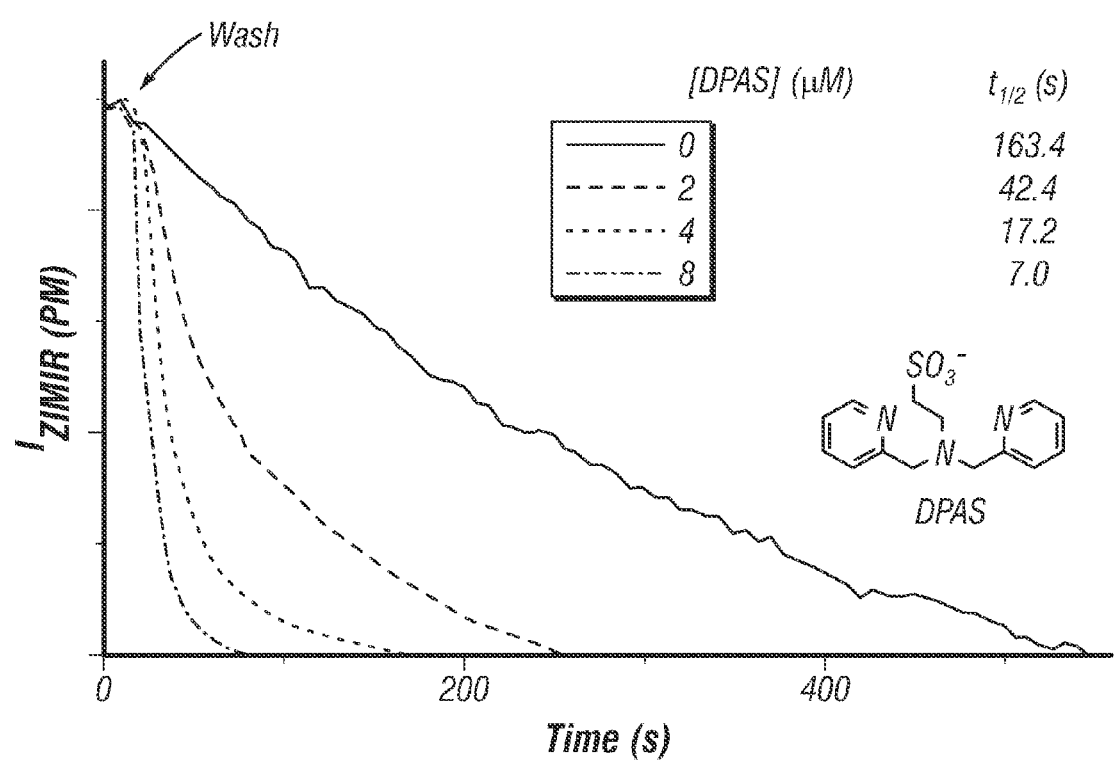
FIGS. 7A-B. DPAS accelerates $Zn^{2+}$ dissipation from membranes and facilitates revealing oscillatory activity of insulin/$Zn^{2+}$ release.
Figure 9:
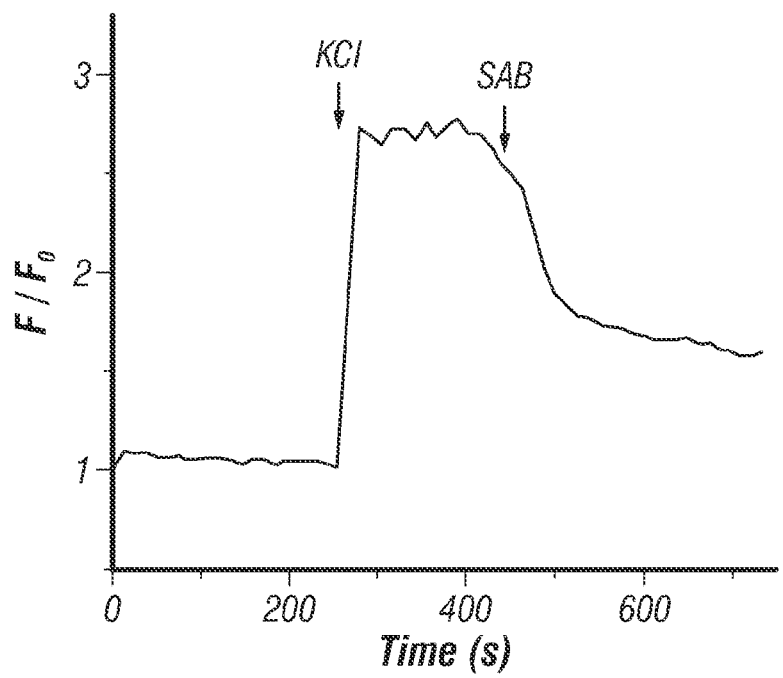
FIG. 9. ZIMIR signal remained elevated after termination of KCl stimulation. After KCl (40 mM) stimulation, MIN6 cells were washed with the secretion assay buffer (SAB) containing 5 mM KCl. EDTA (10 μM) was present throughout the experiment.
Figure 10:
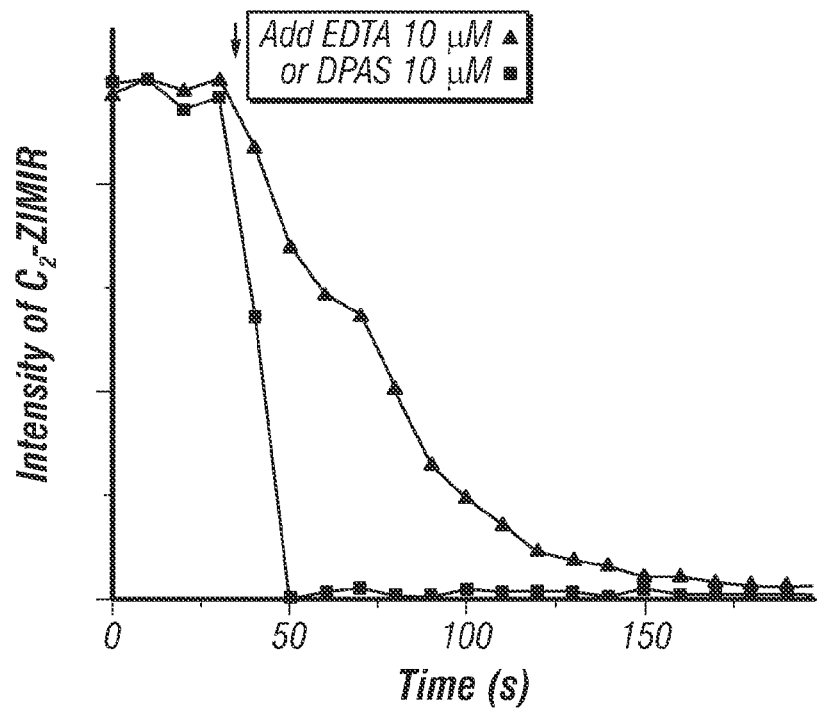
FIG. 10. DPAS chelates $Zn^{2+}$ much faster than EDTA. In this competition assay, fluorescence intensity (Ex 490 nm, Em 525 nm) of ZIMIR-C2 (1 μM) in Hanks Balanced Saline Solution was recorded. The rate of fluorescence intensity decline after adding EDTA or DPAS reflects the kinetics of EDTA/$Zn^{2+}$ or DPAS/$Zn^{2+}$ complexation.

Upon membrane depolarization, ZIMIR signal increased immediately and reached a plateau before it gradually declined (FIGS. 6E-F). Unexpectedly, however, in some occasions, ZIMIR signal remained elevated even after the inventors lowered KCl concentration to the resting level (5 mM) (FIG. 9). This prolonged elevation of fluorescence suggested that $Zn^{2+}$, once released from the insulin granules and complexed by ZIMIR, only gradually dissociated from the membrane-anchored chelators before it escaped into the bulk solution. Since such a slow membrane dissipation of $Zn^{2+}$ could artificially lengthen the duration of the observed insulin/$Zn^{2+}$ release, and could obscure resolving individual episodes of secretory bursts that occur in succession, the inventors tested whether they could accelerate $Zn^{2+}$ dissipation from ZIMIR-labeled membranes by applying a membrane impermeable $Zn^{2+}$ chelator, dipicolylamine N-ethylsulfonate (DPAS, FIG. 7A). DPAS, like other dipicolylamine based chelators, hinds $Zn^{2+}$ with good selectivity against $Ca^{2+}$ and $Mg^{2+}$, and it chelates $Zn^{2+}$ with much faster kinetics than EDTA in physiological salines (FIG. 10). In INS-1 beta cells labeled with ZIMIR, after recording ZIMIR fluorescence in solutions containing ~1 µM of Zn2+, the inventors perifused cells with a nominally $Zn^{2+}$-free solution containing only EDTA (10 µM), or with both EDTA (10 µM) and different concentrations of DPAS. In the absence of DPAS, membrane ZIMIR signal declined slowly upon $Zn^{2+}$ washout (decaying half lifetime=163.4 sec, FIG. 7A). In contrast, DPAS, even at low micromolar concentrations, increased the rate of $Zn^{2+}$ dissipation from the plasma membrane by about one order of magnitude.

Figure 7B:
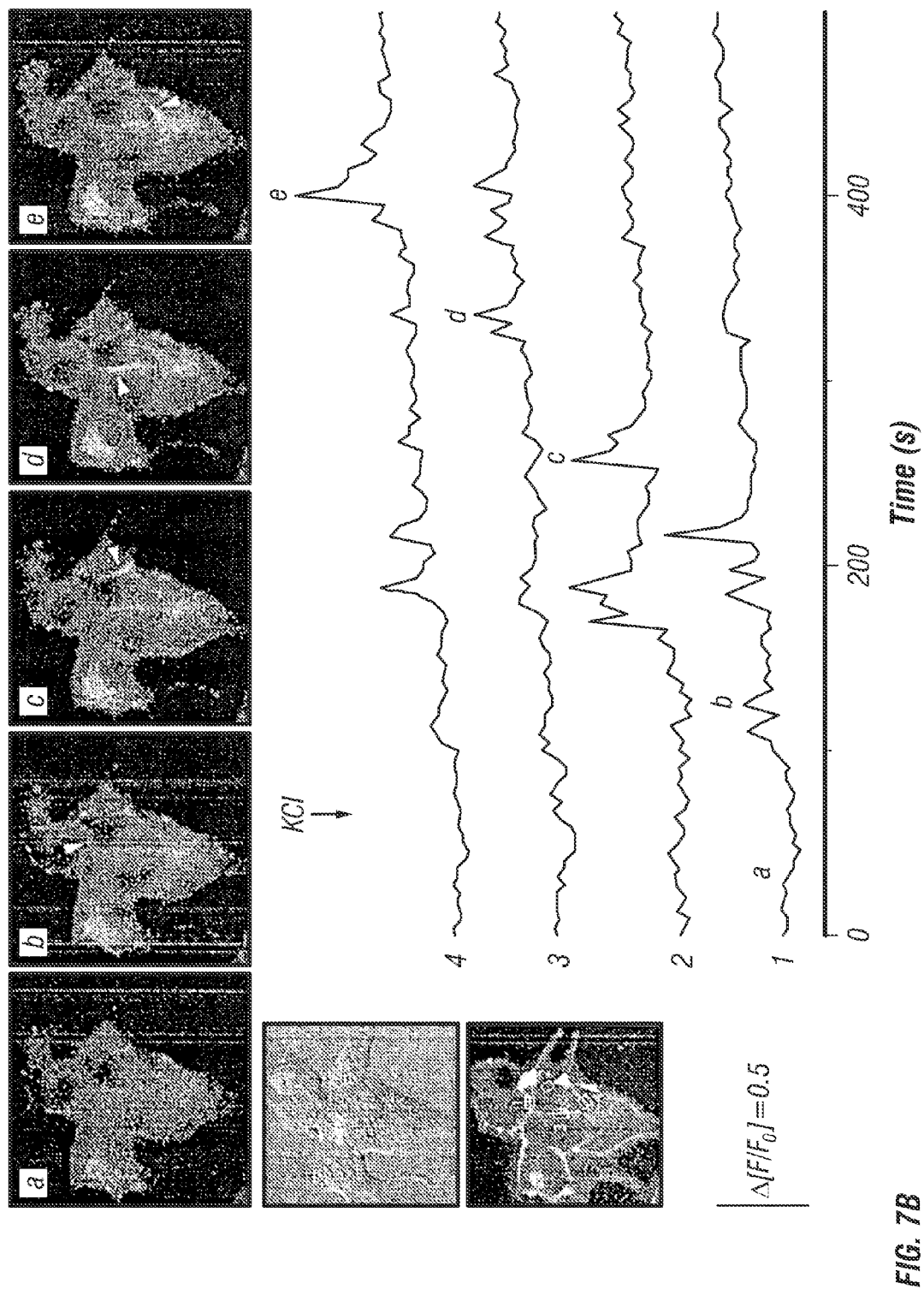

Consistent with the role of DPAS in accelerating $Zn^{2+}$ dissipation into the bulk solution, ZIMIR imaging in the presence of DPAS displayed a more dynamic picture of insulin release activity, revealing repetitive fluorescence spikes along the plasma membranes in both cultured MIN6 cells (FIG. 7B) and in primary human beta cells (data not shown). Interestingly, there appeared to be preferred sites of insulin release along the cell-cell contacts where pulses of insulin release were observed repeatedly. Whether those sites correspond to subcellular domains that favor the formation of readily releasable pools of insulin granules remains an interesting question for future investigation.

Figure 8A:
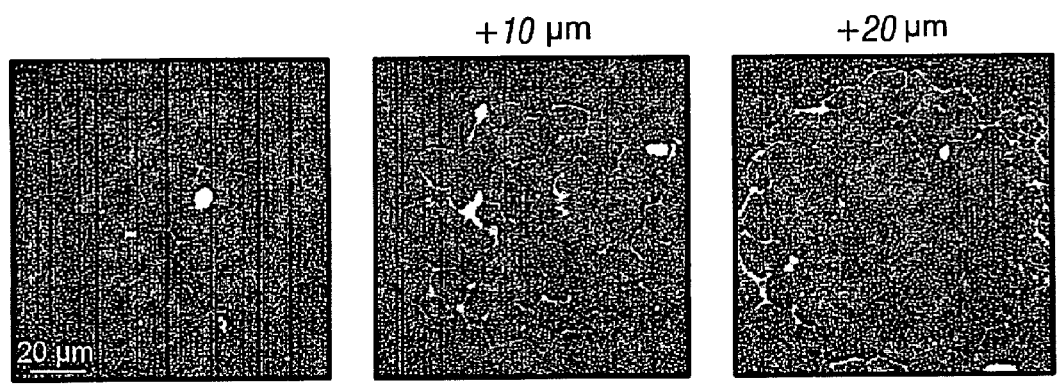
FIGS. 8A-C. Imaging insulin/$Zn^{2+}$ release in islets by confocal laser scanning microscopy.
Figure 8B:
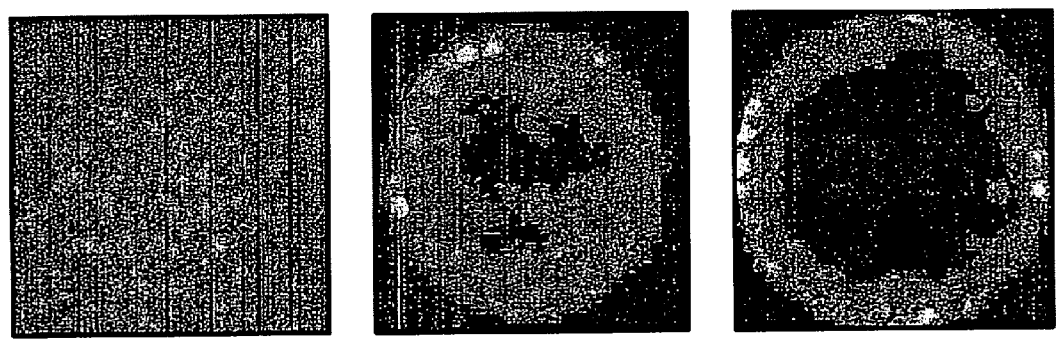
Figure 8C:
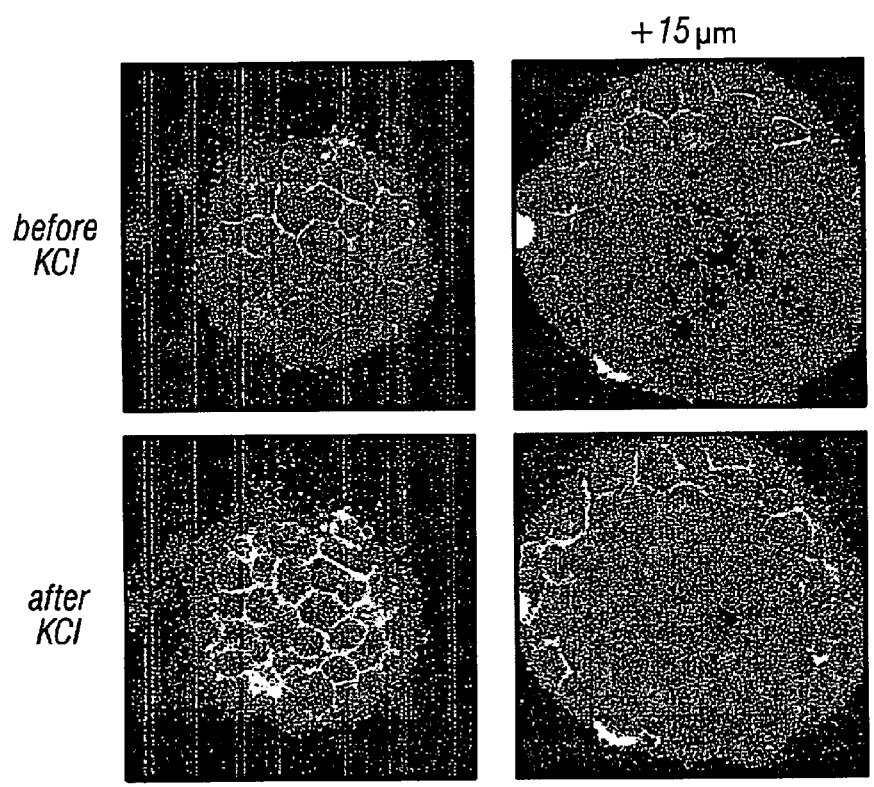
Figure 11:
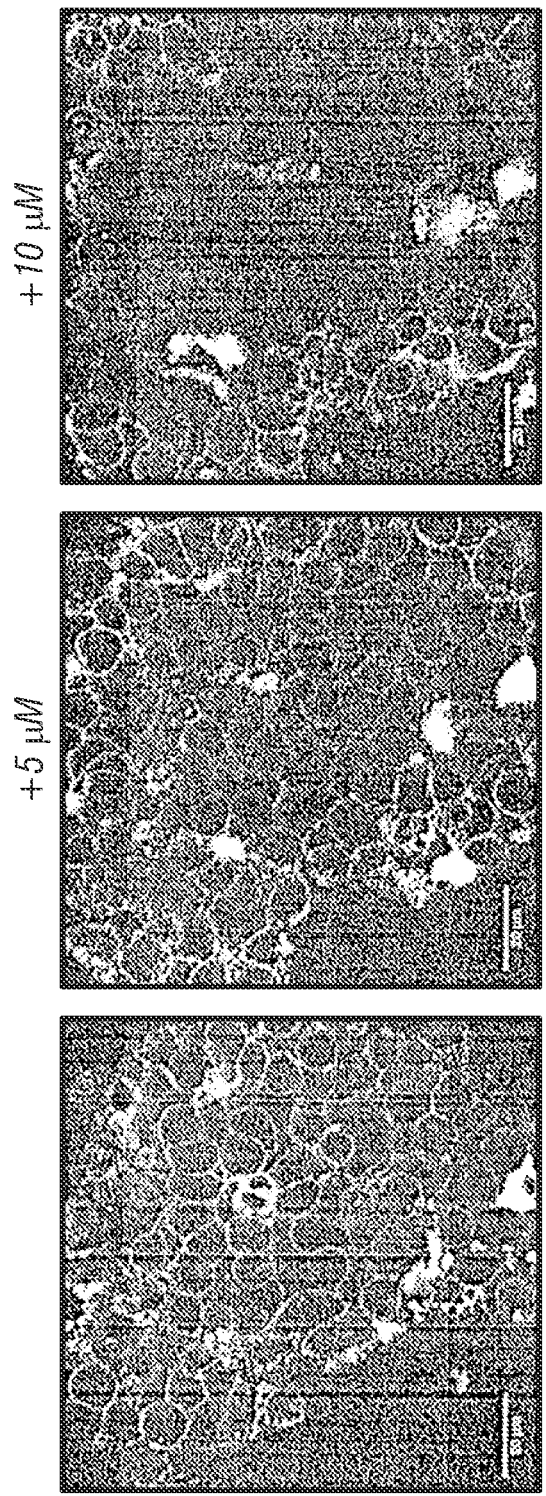
FIG. 11. ZIMIR rapidly labels cells of intact human islets. Representative CLSM images of a ZIMIR labeled human islet at three focal planes 20 μm apart.
Figure 12A:
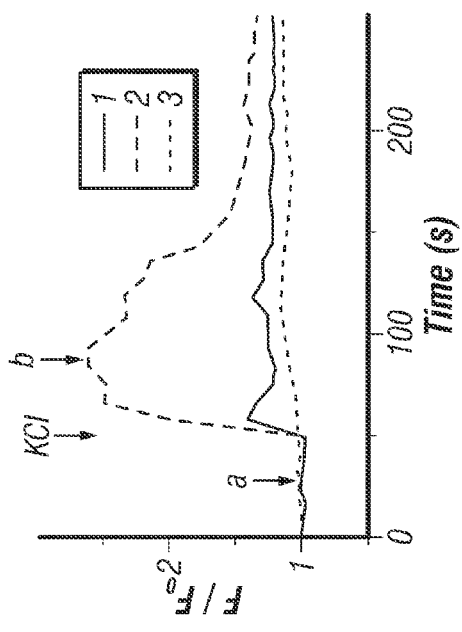
FIGS. 12A-B. Concurrent imaging of insulin/Zn2+ release and [Ca2+]c in MIN6 beta cells. Example ZIMIR fluorescence images (FIG. 12A) and Fura-2 pseudocolor ratio images (FIG. 12B, 340 nm vs. 380 nm excitation) corresponded to time points a & b marked on the time courses. ZIMIR intensity changes were plotted for 3 ROIs, marked as dashed circles in the DIC image and corresponded to the cell-cell contact of a cell doublet (1), the average of cell-cell contacts of a cell triplet (2), and along the plasma membrane of a singlet (3), respectively. Corresponding Fura-2 ratio changes were measured in the bulk cytosol of these three areas.
Figure 12A:
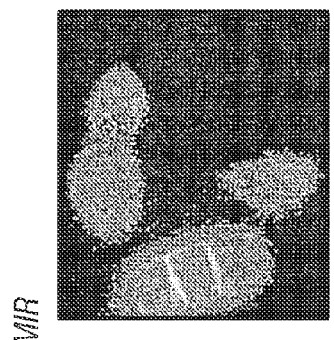
Figure 12B:
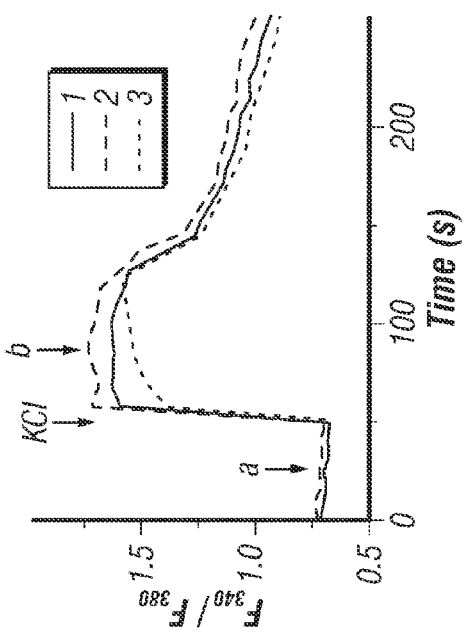
Figure 12B:
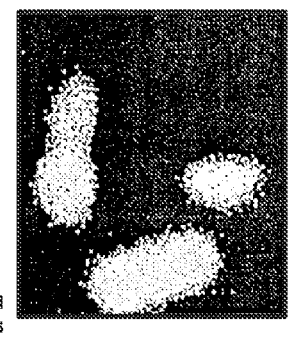

Confocal imaging of ZIMIR uptake and insulin/$Zn^{2+}$ release in pancreatic islets. In addition to cultured cells, ZIMIR also rapidly and noninvasively labels cells in preparations such as dissected pancreatic islets. After loading islets with ZIMIR (2 µM) for 25 min, the inventors applied CLSM to track the distribution of ZIMIR in three dimensions (3D). They observed that ZIMIR was taken up by cells throughout the islets, from the mantle to the core (FIG. 8A, mouse islets; and FIG. 11, human islets). In contrast, loading cells with cytosolic dyes such as calcein/AM only labeled cells of the superficial layers (FIG. 8B). The result confirmed that ZIMIR readily diffused through the interstitial space to reach interior cells, whereas calcein/AM was trapped by cells in the outer layer, unable to penetrate any deeper. After labeling, the inventors depolarized cells with high concentration of KCl. A robust and synchronized enhancement of ZIMIR fluorescence was detected in many cells in the islet (FIG. 8C), demonstrating ZIMIR's ability to capture the dynamics of insulin granule release at cellular and sub-cellular resolution in physiological preparations or tissues.

VIII. References

The following references, to the extent that they provide exemplary procedural or other details supplementary to those set forth herein, are specifically incorporated herein by reference.

Bedrossian, *Diagn. Cylopathol.*, 18(2):141-149, 1998.
Birinyi et al. *J. Comp. Neurol.*, 433:208-221, 2001.
Chimienti et al., *Diabetes*, 53:2330-2337, 2004.
Dakin and Li, *Cell Calcium*, 42:291-301, 2007.
Falkmer and Pihl, *Diabetologia*, 4:239-243, 1968.
Frederickson et al., *J. Histochem. Cytochem.*, 35:579-583, 1987.
Frederickson et al., *Nat. Rev. Neurosci.*, 6:449-462, 2005.
Gee et al., *J. Am. Chem. Soc.*, 124:776-778, 2002.
Giblin et al., *J. Histochem. Cytochem.*, 54:311-316, 2006.
Goldberg et al., *Klin. Lab. Diagn.*, 25-27, 1993.
Guo et al., *Nat. Methods*, 5:835-841, 2008.
Gustafson, *Lab. Invest.*, 17:588-598, 1967.
*Handbook of Pharmaceutical Salts: Properties, and Use* (Stahl & Wermuth) Eds., Verlag Helvetica Chimica Acta, 2002.
Haug, *Histochemie*, 8:355-368, 1967.
Hauser and Tsien, *Proc. Natl. Acad. Sci. USA*, 104:3693-3697, 2007.
Hirano et al. *J. Amer. Chem. Soc.*, 122:12399-12400, 2000.
Ho et al., *J. Immunol.*, 172:7750-7760, 2004.
Ieshchenko et al., *Lik Sprava*, 86-88, 1994.
Kasai et al., *J., Physiol.*, 568:891-903, 2005.
Komatsu et al., *J. Am. Chem. Soc.*, 127:10197-10204, 2005.
Kristiansen et al., *Histochem. Cell Biol.*, 115:125-129, 2001.
Li et al., *Nat. Protoc.*, 4:1649-1652, 2009.
Liang et al., *Green Chem.*, 7:410-412, 2005.
Michael et al., *Diabetes* 55, 600-7, 2006.
Michael et al., *Diabetes*, 56:1277-1288, 2007.
Miyazaki et al., *Endocrinology*, 127:126-132, 1990.
Muller and Geyer, *Gegenbaurs Morphol. Jahrb.*, 113:70-77, 1969.
Nagamatsu, *Endocr. J.*, 53:433-440, 2006.
Neuschl et al., *Molecules*, 12:49-59, 2007.
Nicolson et al., *Diabetes*, 58:2070-2083, 2009.
Ohara-Imaizumi et al., *J. Biol. Chem.*, 277:3805-3808, 2002.
Qian et al., *Anal. Chem.*, 75:3468-3475, 2003.
Ravier and Rutter, *Diabetes*, 54:1789-1797, 2005.
Rorsman and Renstrom, *Diabetologia*, 46:1029-1045, 2003.
Rungby, *Diabetologia*, 53:1549-1551, 2010.
Sorensen et al., *Prostate*, 31:125-130, 1997.
Thorlacius-Ussing, *Neuroendocrinology*, 45:233-242, 1987.
Wijesekara et al., *Diabetologia*, 2010.
Zhang et al., *J. Org. Chem.*, 73:734-737, 2008.

What is claimed is:

1. A method of detecting zinc ion ($Zn^{2+}$) release by a cell comprising:
(a) contacting a cell with a compound having the formula:

[Chemical structure]

wherein
$R_1$ and $R_4$ are independently H, or —$CH_2(CH_2)_aCOOH$, $CH_2(CH_2)_bSO_3H$, wherein
a = is 0, 1 or 2 and b, 1, 2 or 3;
$R_2$ and $R_3$ are independently H, or linear or branched $C_{1-20}$ alkyl;
$R_5$ and $R_6$ are independently H, F, Cl, Br;
R7 is H, or linear or branched $C_{1-4}$ alkyl or acetate;
R8 and R9 are independently H, or linear or branched $C_{1-4}$ alkyl or acetate; and
m is 1, 2 or 3;
n is 1, 2, 3 or 4; and
o is 1,2, 3 or 4;
and pharmaceutically acceptable salts thereof, and
(b) detecting fluorescence of said compound following zinc release by said cell and binding of zinc by said compound.

2. The method of claim 1, wherein said cell is pancreatic beta cell, a submandibular salivary gland cell, a prostate epithelial cell, a paneth cell, a mast cell, a granulocyte, a pituitary cell, a or a CNS neuron.

3. The method of claim 1, wherein detecting comprises confocal laser scanning microscopy, two photon laser scanning microscopy, or total internal reflection fluorescence microscopy.

4. The method of claim 1, wherein said cell is an isolated cell.

5. The method of claim 1, wherein said cell is in an intact tissue.

6. The method of claim 5, wherein said tissue is an isolated pancreatic islet.

7. The method of claim 1, further comprising detecting fluorescence at multiple time points.

8. The method of claim 1, further comprising stimulating said cell with a zinc ion release agent.

9. The method of claim. 1, wherein the concentration of said compound is between 1 nM and 100 μM.

10. The method of claim 1, wherein the concentration is between 5 nM and 1 μM.

11. The method of claim 1, wherein $R_5$, $R_6$, $R_7$, $R_8$ and $R_9$ are H, in and n are 1 and o is 2.

12. The method of claim 11 wherein $R_1$ and $R_4$ are the same.

13. The method of claim 11, wherein $R_2$ and $R_3$ are the same.

14. The method of claim 12, wherein $R_2$ and $R_3$ are the same.

15. The method of claim 14, wherein $R_1$ and $R_4$ are —$CH_2COOH$, and $R_2$ and $R_3$ are —$CH_2CH_3$ or —$(CH_2)_{11}CH_3$.

16. A compound having the formula:

[Chemical structure]

wherein
$R_1$ and $R_4$ are independently H, or —$CH_2(CH_2)_aCOOH$, $CH_2(CH_2)_bSO_3H$, wherein a is 0, 1 or 2 and b 1, 2 or 3;
$R_2$ and $R_3$ are independently H, or linear or branched $C_{1-20}$ alkyl;
$R_5$ and $R_6$ are independently H, F, Cl, Br;
R7 is H, or linear or branched $C_{1-4}$ alkyl or acetate;
R8 and R9 are independently H, or linear or branched $C_{1-4}$ alkyl or acetate; and
m is 1, 2 or 3;
n is 1, 2, 3 or 4; and
o is 1 2, 3 or 4;
and pharmaceutically acceptable salts thereof.

17. The compound of claim 16, wherein $R_5$, $R_6$, $R_7$, $R_8$ and $R_9$ are H, m and n are 1 and o is 2.

18. The compound of claim 17, wherein $R_1$ and $R_4$ are the same.

19. The compound of claim 17, wherein $R_2$ and $R_3$ are the same.

20. The compound of claim 18, wherein $R_2$ and $R_3$ are the same

21. The compound of claim 20, wherein $R_1$ and $R_4$ are —$CH_2COOH$ and $R_2$ and $R_3$ are —$CH_2CH_3$ or —$(CH_2)_{11}CH_3$.

22. A ligand metal complex having the formula:

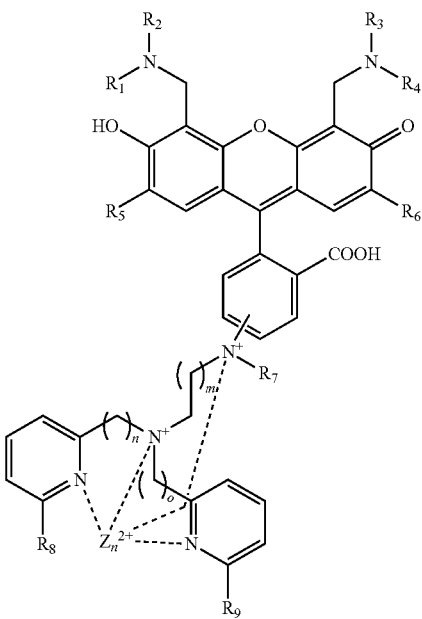

wherein
$R_1$ and $R_4$ are independently H, or —$CH_2(CH_2)_a COOH$, $CH_2(CH_2)_b SO_3H$, wherein a is 0, 1 or 2 and b 1, 2 or 3;

$R_2$ and $R_3$ are independently H, or linear or branched $C_{1-20}$ alkyl;

$R_5$ and $R_6$ are independently H, F, Cl, Br;

R7 is H, or linear or branched $C_{1-4}$ alkyl or acetate;

R8 and R9 are independently H, or linear or branched $C_{1-4}$ alkyl or acetate; and m is 1, 2 or 3;

n is 1, 2, 3 or 4; and o is 1, 2, 3 or 4;

and pharmaceutically acceptable salts thereof.

23. The ligand metal complex of claim 22, wherein $R_5$, $R_6$, $R_7$, $R_8$ and $R_9$ are H, m and n are 1 and o is 2.

24. The ligand metal complex of claim 23, wherein $R_1$ and $R_4$ are the same.

25. The ligand metal complex of claim 23, wherein $R_2$ and $R_3$ are the same.

26. The ligand metal complex of claim 24. wherein $R_2$ and $R_3$ are the same

27. The ligand metal complex of claim 26, wherein $R_1$ and $R_4$ are —$CH_2COOH$ and $R_2$ and $R_3$ are —$CH_2CH_3$ or —$(CH_2)_{11}CH_3$.

* * * * *

UNITED STATES PATENT AND TRADEMARK OFFICE
CERTIFICATE OF CORRECTION

PATENT NO. : 8,530,183 B2
APPLICATION NO. : 13/158011
DATED : September 10, 2013
INVENTOR(S) : Li et al.

Page 1 of 1

It is certified that error appears in the above-identified patent and that said Letters Patent is hereby corrected as shown below:

In the Claims

Claim 1, column 23, line 35, delete "a = is" and insert --a is-- therefor.

Claim 1, column 23, line 35, delete "b, 1," and insert --b is 1,-- therefor.

Claim 2, column 23, line 53, delete "a or a" and insert --or a-- therefor.

Claim 11, column 24, line 6, delete "in" and insert --m-- therefor.

Claim 16, column 24, line 45, delete "b 1," and insert --b is 1,-- therefor.

Claim 20, column 24, line 64, after "same" insert a --.--.

Claim 22, column 26, line 3, delete "b 1," and insert --b is 1,-- therefor.

Claim 26, column 26, line 23, after "same" insert a --.--.

Claim 27, column 26, line 25, delete "$_{and\ R_3}$" and insert --and $R_3$-- therefor.

Signed and Sealed this
Tenth Day of December, 2013

Margaret A. Focarino
*Commissioner for Patents of the United States Patent and Trademark Office*